US007994369B2

(12) United States Patent
Scheibel et al.

(10) Patent No.: US 7,994,369 B2
(45) Date of Patent: Aug. 9, 2011

(54) SPECIFIC POLYBRANCHED POLYALDEHYDES, POLYALCOHOLS, AND SURFACTANTS, AND CONSUMER PRODUCTS BASED THEREON

(75) Inventors: Jeffrey John Scheibel, Loveland, OH (US); Robert Edward Shumate, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/564,456

(22) Filed: Sep. 22, 2009

(65) Prior Publication Data

US 2010/0105958 A1    Apr. 29, 2010

Related U.S. Application Data

(60) Provisional application No. 61/098,879, filed on Sep. 22, 2008.

(51) Int. Cl.
*C07C 47/12* (2006.01)
*C07C 31/18* (2006.01)
*C11D 3/02* (2006.01)

(52) U.S. Cl. .................. 568/494; 568/853; 510/108
(58) Field of Classification Search .................. 568/494, 568/853; 510/108
See application file for complete search history.

(56) References Cited

U.S. PATENT DOCUMENTS

| | | | |
|---|---|---|---|
| 3,240,816 A | 3/1966 | Hurwitz et al. | |
| 3,420,898 A | 1/1969 | Winkle et al. | |
| 3,641,155 A | 2/1972 | Tilford et al. | |
| 4,133,779 A | 1/1979 | Hellyer et al. | |
| 4,228,042 A | 10/1980 | Letton | |
| 4,239,660 A | 12/1980 | Kingry | |
| 4,260,529 A | 4/1981 | Letton | |
| 4,454,145 A | 6/1984 | Cristofori et al. | |
| 4,483,779 A | 11/1984 | Llenado et al. | |
| 4,483,780 A | 11/1984 | Llenado | |
| 4,520,214 A | 5/1985 | Vora | |
| 4,523,048 A | 6/1985 | Vora | |
| 4,565,647 A | 1/1986 | Llenado | |
| 4,605,783 A | 8/1986 | Zinnen | |
| 4,681,704 A | 7/1987 | Bernardino et al. | |
| 4,695,560 A | 9/1987 | Gattuso et al. | |
| 4,761,509 A | 8/1988 | Vora et al. | |
| 4,806,661 A | 2/1989 | Cohen | |
| 5,332,528 A | 7/1994 | Pan et al. | |
| 5,510,510 A | 4/1996 | Patel et al. | |
| 5,576,282 A | 11/1996 | Miracle et al. | |
| 5,780,694 A | 7/1998 | Singleton | |
| 5,849,960 A | 12/1998 | Singleton et al. | |
| 5,980,931 A | 11/1999 | Fowler et al. | |
| 6,004,922 A | 12/1999 | Watson et al. | |
| 6,008,181 A | 12/1999 | Cripe et al. | |
| 6,020,303 A * | 2/2000 | Cripe et al. ................ 510/503 | |
| 6,022,844 A | 2/2000 | Baillely et al. | |
| 6,060,443 A * | 5/2000 | Cripe et al. ................ 510/426 | |
| 6,093,856 A | 7/2000 | Cripe et al. | |
| 6,121,165 A | 9/2000 | Mackey et al. | |
| 6,136,769 A | 10/2000 | Asano et al. | |
| 6,150,322 A * | 11/2000 | Singleton et al. .......... 510/426 | |
| 6,153,577 A | 11/2000 | Cripe et al. | |
| 6,221,825 B1 | 4/2001 | Williams, Jr. et al. | |
| 6,222,077 B1 | 4/2001 | Singleton | |
| 6,239,093 B1 | 5/2001 | Foley et al. | |
| 6,274,540 B1 | 8/2001 | Scheibel et al. | |
| 6,306,812 B1 | 10/2001 | Perkins et al. | |
| 6,326,348 B1 | 12/2001 | Vinson et al. | |
| 6,335,312 B1 * | 1/2002 | Coffindaffer et al. ........ 510/159 | |
| 6,482,994 B2 | 11/2002 | Scheper et al. | |
| 6,596,680 B2 | 7/2003 | Kott et al. | |
| 6,627,778 B2 | 9/2003 | Xu et al. | |
| 6,844,309 B1 | 1/2005 | Sivik et al. | |
| 6,872,556 B2 | 3/2005 | Hoshino et al. | |
| 6,908,894 B2 | 6/2005 | Kott et al. | |
| 6,956,017 B1 | 10/2005 | Catalan et al. | |
| 7,183,446 B2 * | 2/2007 | Zeller et al. ................ 568/876 | |
| 7,399,323 B2 * | 7/2008 | Renninger et al. .......... 44/385 | |
| 2008/0083158 A1 | 4/2008 | Renninger et al. | |
| 2008/0118443 A1 | 5/2008 | Jaunky et al. | |
| 2010/0137649 A1 | 6/2010 | Scheibel et al. | |

FOREIGN PATENT DOCUMENTS

| | | |
|---|---|---|
| CN | 1032157 A | 4/1989 |
| EP | 0542217 A2 | 5/1993 |
| JP | 48040705 | 6/1973 |
| JP | 48033722 B | 10/1973 |
| JP | 52031841 | 3/1977 |
| WO | WO 98/35002 A1 | 8/1998 |
| WO | WO 98/35003 A1 | 8/1998 |
| WO | WO 98/35004 A1 | 8/1998 |
| WO | WO 98/35005 A1 | 8/1998 |
| WO | WO 98/35006 A1 | 8/1998 |
| WO | WO 99/05244 A1 | 2/1999 |
| WO | WO 00/47708 A1 | 8/2000 |

OTHER PUBLICATIONS

PCT International Search Report, date mailed: Mar. 25, 2010, 17 pages.
Scheibel JSD:The Evolution of Anionic Surfactant Technology to Meet the Requirements of the Laundry Detergent Industry. Journal of Surfactants and Detergents. vol. 7, No. 4, Oct. 2004. pp. 319-328.
Dietmar Appelhans, et al.: Syntheses with Aliphatic Dialdehydes, XLVI. Synthesis and Reactions of 2,2-Dialkyl-Substituted Malonaldehydes and Their Semi (Ethylene Acetals. Liebigs Annalen: Organic and Bioorganic Chemistry, VCH Publishers, US vol. 11, Oct. 22, 1997. pp. 2385-2392.
Melissa L. Grachan et al.: Enantioselective Catalytic Carbonyl Ene Cyclization Reactions. Angewandte Chemie International Edition, VCH Verlag, Weinheim, DE vol. 47, No. 8, Feb. 8, 2008. pp. 1469-1472.
Roger K Murray, et al.: Roger K. Murray et al.: On the Photochemistry of 1-Oxaspiro(2.n) alkan-5-ones. Journal of Organic Chemistry, American Chemical Society, Easton.; US vol. 42, No. 25, Jan. 1, 1977. pp. 3994-3997.

(Continued)

*Primary Examiner* — Sikarl Witherspoon
(74) *Attorney, Agent, or Firm* — Stephen T. Murphy; Steven W. Miller; Leonard W. Lewis

(57) ABSTRACT

Acyclic polyaldehydes and polyalcohols having 11, 16 or 21 carbon atoms and comprising at least two aldehyde or hydroxyl alcohol groups, at least three branches, and three or less carbon-carbon double bonds.

15 Claims, No Drawings

OTHER PUBLICATIONS

Climent M J et al.: Aldol Condensation on Solid catalysts: A Cooperative Effect between Weak Acid and Base Sites. Advanced Synthesis & Catalysis, Wiley VCH Verlag, Weinheim, DE vol. 344, No. 10, Jan. 1, 2002 pp. 1090-1096.

Chkir and D Lelandais M: Electrochemical synthesis of compounds of general formula(Rich2cr2y)2 Journal of the chemical Society. Letchworth, GB Jan. 1, 1971. pp. 1369-1370.

Foca C M et al.: Hydroformylation of myrcene: metal and ligand effects in the hydroformylation of conjugated dienes New Journal of Chemistry, Royal Society of Chemistry, GB vol. 27, 3. Feb. 3, 2003. pp. 533-539.

Soicht Sakane et al.: Asymmetric Clclization of Unsaturated Aldehydes Catalyzed by a Chiral Lewis Acid. Tetrahedron Letters, Elsevier, Amsterdam, NL vol. 26, No. 45, Jan. 1, 1985. pp. 5535-5538.

Takashi Mino et al. Hydrolysis of Beta, gamma-Unsaturated Aldehyde Dimethylhydrazones with Copper Dichloride: A New Synthesis of Lavandulol. Journal of Organic Chemistry, American Chemical Society. vol. 62, No. 3. Jan. 1, 1997. pp. 734-735.

Olga B Morozova et al. 1H and 13C Nuclear Polarization in Consecutive Biradicals during the Photolysis of 2,2,12,12-Tetramethylcyclododecanone. Journal of Physical Chemistry. A Molecules, Spectroscopy, Kinetics, Environment and General Theory, vol. 101, No. 4, Jan. 1, 1997. pp. 399-406.

Yongsong H. et al. Novel Unsaturated Triterpenoid Hydrocarbons from Sediments of Sacred Lake, Mt. Kenya, Kenya. Tetrahedron, Elsevier Science Publishers, Amsterdam, NL. vol. 52, No. 20, May 13, 1996. pp. 6973-6982.

Mallyabaeva M I et al.: New method for the synthesis of (3r,7R)-hexahydrofarnesyl dromide based on the microwave-activated regloselective enolization of homochiral phytone. Russian Chemical Bulletin, Kluwer Academic Publishers-Plenum Publishers, NE vol. 56, No. 12, Sep. 20, 2008. pp. 2443-2447.

Odinokov V N. et al: New Enantiospecific Synthesis of (+)-(2R,6R)-(+)-2,6,10-Trimethylunde can-l-ol for Constructing the Side Chain of Natural (2R,4'R,8'R)-(+)-[alpha]-Tocopherol (Vitamin E). Doklady Chemistry, Kluwer Academic Publishers-Plenum Publishers, NE vol. 403, No. 4-6. Aug. 1, 2005. pp. 144-147.

Hird Nicolas W et al.: The total synthesis of 10-(R,S)-C30 botryococcene and botryococcane and a new synthesis of a general intermediate to the botryococcene family. Tetrahedron Letters, Elsevier, Amsterdam, NL vol. 30, No. 36. Jan. 1, 1989. pp. 4867-4870.

Uemoto K et al.: Prenyl and geranyl phenyl sulfone, a new carbon nucleophile for Mitsunobu-type alkylation. Tetrahedron Letters, Elsevier, Amsterdam, NL, vol. 42, No. 5, Jan. 29, 2001. pp. 905-907.

Evans David A et al.: Synthetic Studies in the lysocellin family of polyether antibiotics. The total synthesis of ferensimyc in B. Journal of the American Chemical Society, American Chemical Society, New York, USA, vol. 113, No. 20, Jan. 1, 1991. pp 7613-7630.

Poppe L. et al.: Convenient Synthetic Route to (+)- Faranal and (+)-13- Nonfaranal the Trail Pheromone or Pharoah's ant and its Congener. Tetrahedron, Elsevier Science Publishers, Amsterdam, NL. vol. 44, No. 5, Jan. 1, 1988, pp. 1477-1487.

Noal Cohen and Beatrice Schaer: Synthesis of (2RS,4'R,8'R)-a—Tocopherol and Related Compounds via a 2-Chlorochroman, Journal of Organic Chemistry, American Chemical Society, Easton, US. vol. 57, No. 21, Jan. 1, 1992, pp. 5783-5785.

Dietmar Appelhans et al: Syntheses with Aliphatic Dialdehydes, XLVI. Sythesis and Reactions of 2,2-Dialkyl-Sustituted Malonaldehydes and Their Semi(Ethylene Acetals) Liebigs Annalen:Organic and Bioorganic Chemistry, VCH Publishers, US vol. 11, 22. Oct. 22, 1997. pp. 2385-2392.

Hiroshi Ohrui et al.: Development of Highly Potent D-Glucosmine-Based Chiral Fluorescent Labeling Reagents and a Microwave-Assisted Beta-Selective Glycosidation of a Methyl Glycoside Reagent, Bioscience, Biotechnology, amd Agrochemistry, Tokyo, Japan. vol. 69, No. 5. May 1, 2005. pp. 1054-1057.

Paulo H G Zarbin et al.: Synthesis and Biological Activity of Methyl 2,6,10- Trimethyldodecano Ate and Methyl 2,6,10-Trimethyltridecanoate: Male-Produced Sexual Pheromones of Stink Bugs Euschistus heros and Piezodorus guildin11. Journal of Chemical Ecology, Plenum Publishing Corp., US. vol. 26, No. 12. Jan. 1, 2000. pp. 2737-2746.

Erwan Saouter: Natural and Synthetic Surfactants. Which one is better? Internet Citation. Oct. 23, 2003, pp. 13PP, XP007911908. Retrieved from the Internet: URL:http://www.scienceinthebox.com/en_UK/pdf/52_oleo_Article%204.pdf.

Francis J McQuillin and David George Parker: Complexing of terpenese with transition metals. Part V. Reactions of 3,7-dimethylocta-1,6-diene and of 7-methoxy-3, 7-dimethyloct-l-ene with rhodium (III) and thallium (III). Journal of the Chemical Society, Perkin Transactions 1, Chemical Society, Letchworth; GB. vol. 20 1. Jan. 1, 1975. pp. 2092-2096.

T. Chandiran and S. Vancheesan: Hydrogenation of Conjugated dienes catalysed by n6-arenetricarbonylchromium complexes. Journal of Molecular Catalysis, 88. pp. 31-42.

Marcelo G. Speziali, et al.: Selective hydrogenation of myrcene catalyzed by complexes of ruthenium, chromium, iridium and rhodium. Journal of Molecular Catalysis A: Chemical 239 (2005) pp. 10-14.

R. Haubaut, et al.: Selective Hydrogenation of Heavy Polyunsaturated Molecules on Copper-Chromium Catalysts. Journal of Molecular Catalysis, 55 (1989) pp. 170-183.

Patricia A. Robles-Dutenhefner et al.: Selective hydrogenation of myrcene catalyzed by sol-gel $Pd/SiO_2$ Applied Catalysis A: General 295 (2005) 52-58.

* cited by examiner

SPECIFIC POLYBRANCHED POLYALDEHYDES, POLYALCOHOLS, AND SURFACTANTS, AND CONSUMER PRODUCTS BASED THEREON

CROSS-REFERENCES TO RELATED APPLICATIONS

This application claims priority under 35 U.S.C. §119(e) to U.S. Provisional Application Ser. No. 61/098,879 filed Sep. 22, 2008.

FIELD OF THE INVENTION

The present invention relates to certain novel aldehydes, detergent alcohols, surfactants and consumer products such as laundry products, personal care products, dishcare products, shampoo products and hard surface cleaning products, and the like comprising said surfactant compositions. Processes to make the novel aldehydes, alcohols and surfactants are also disclosed.

BACKGROUND OF THE INVENTION

Surfactants, even today, are the single most important cleaning ingredient in laundry and household cleaning products. Anionic surfactants, as a class, are the largest in terms of worldwide consumption and typically are used at levels as high as 30 to 40% of the detergent formulation. Evolution of this class sometimes called "mainframe surfactants" has always been slow due to the long development times and high capital investment costs in this multibillion pound a year commodity industry. Changes are often driven by changing consumer needs or habits such as the development of new fabric types which may require lower wash temperatures and gentle wash cycles or the fast paced society we now live in where shorter wash times are becoming the norm. All of the above factors have played a role in past developments of new anionic surfactants. As a result of the need for surfactants with properties that lend themselves to higher tolerance to precipitation with calcium and magnesium in hard water as well as improved cleaning in the colder wash temperatures and shorter wash cycle there has been in recent years several chemical developments which have led to the introduction of specific methyl and ethyl branched surfactants. Examples of such developments are described in the article by J. Scheibel, Journal of Surfactants and Detergents, *"The Evolution of Anionic Surfactant Technology to Meet the Requirements of the Laundry Detergent Industry"*, volume 7, number 4, October, 2004 ("Scheibel JSD Article" hereinafter) which defines the need and developments of these branched surfactant technologies. The technologies indicate the need for minimization of the branching to provide efficient surfactants with good biodegradability.

Highly branched surfactants have been derived from tetrapropylene and were called alkylbenzene sulfonates or "HARD ABS". Hard ABS had very complex branching structures with 3 or 4 branches per molecule. The structure below illustrates one example of a hard ABS molecule. The illustration shows four branches with methyl and ethyl branching in quaternary as well as geminal branching.

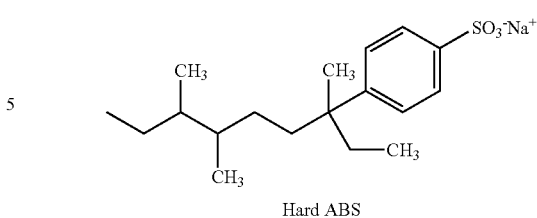

Hard ABS

Hard ABS was found to be significantly less biodegradable than linear alternatives. Alcohol es derived from these highly branched tetrapropylene feedstocks had similar problems as the hard ABS, including inhibited biodegradability. As such the hard ABS and related alcohol es had limited use in laundry or other consumer products.

One example of a currently marketed branched surfactants used in consumer products is a lightly branched alkyl sulfate and is called "HSAS" for highly soluble alkyl sulfate. HSAS is illustrated in the Scheibel JSD article and other external papers HSAS is derived from petroleum feedstocks. The material's light branching provides high solubility, hardness tolerance and good performance.

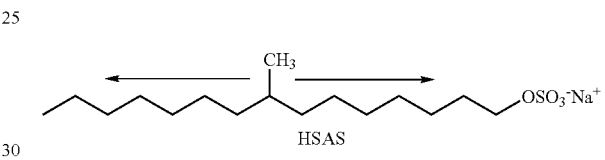

HSAS

Thus, although this surfactant and others are designed to meet the needs of consumers today for cold water cleaning, the challenge remains to provide alternative branched surfactants from non petroleum sources for future sustainability for the detergent industry as well as other industries that rely on surfactant technology and prefer branched materials with the properties of HSAS.

Processes are disclosed herein to make the novel aldehydes, alcohols and surfactants useful in the formulation of consumer products such as personal care products and laundry and cleaning products.

SUMMARY OF THE INVENTION

Described herein is an acyclic aldehyde having either 16 or 21 carbon atoms comprising at least three branches and three or less carbon-carbon double bonds which is a useful raw material for the preparation of detergent surfactants and specific embodiments thereof.

Also described is a detergent alcohol composition comprising at least one acyclic alcohol having 16 carbon atoms comprising at least three branches wherein the branches are methyl, ethyl or mixtures thereof.

A surfactant composition comprising one or more surfactant derivatives of isomers of acyclic detergent alcohol having 11, 16, or 21 carbon atoms and two, three, four or five methyl or ethyl branches or mixtures thereof is also described.

A process for preparing a detergent alcohol mixture comprising the steps of (a) providing one or more poly-branched poly-olefins, wherein the poly-branched poly-olefins must contain one non-branched terminal olefin and one or more additional branched olefins in the molecule; (b) hydroformylating said poly-branched poly-olefins to produce a poly-branched olefin containing aldehyde product with one or more olefins or mixture thereof, utilizing a catalyst selected from the group consisting of modified or unmodified Group IX transition metals, and process conditions comprising a process temperature ranging from about 50° C. to about 130° C., a hydrogen to carbon monoxide mole ratio ranging from about 0.25:1 to about 4:1, and a total pressure ranging from about 300 psig to about 2000 psig; (c) reducing the aldehyde product of step (b) in the presence of hydrogen and a hydrogenation catalyst, utilizing process conditions comprising a process temperature ranging from about 20° C. to about 130° C., and a hydrogen pressure ranging from 100 psig to about 2000 psig to form a poly-branched detergent alcohol mixture; and (d) removing said poly-branched alcohol mixture from said catalyst.

A process for preparing a detergent alcohol mixture, said process comprising the steps of (a) providing poly-branched poly-olefins comprising one non-branched terminal olefin and one or more additional branched olefins in the molecule; (b) hydroformylating and reducing said poly-branched poly-olefin utilizing a catalyst selected from specific modified Group IX transition metals and process conditions comprising a process temperature ranging from about 90° C. to about 200° C., a hydrogen to carbon monoxide mole ratio ranging from about 2 to 1 to about 5 to 1, and a total pressure ranging from about 300 psig to about 2000 psig; and (c) removing said alcohol composition from said catalyst.

The present invention relies on an unexpected discovery that detergent alcohols and derivatives with two or more branches can have both good biodegradability, high solubility in cold hard water, highly efficient in combination with other detergent ingredients such as co-surfactants, enzymes, builders, chelants and cleaning polymers. Furthermore, processes will be defined which provide improved synthetic efficiency over production of other branched surfactants made from petroleum feedstocks.

DETAILED DESCRIPTION OF THE INVENTION

The present invention relates to a process for preparing a detergent alcohol mixture comprising the steps of:

a. providing one or more poly-branched poly-olefins, wherein the poly-branched poly-olefins must contain one non-branched terminal olefin and one or more additional branched olefins in the molecule;

b. hydroformylating the poly-branched poly-olefins to produce a poly-branched olefin containing aldehyde product with one or more olefins or mixture thereof;

c. reducing the aldehyde product of step (b) in the presence of hydrogen and a hydrogenation catalyst; and d. removing the resulting poly-branched alcohol mixture from said catalyst.

One embodiment of the present process includes the hydroformylating step and the reducing step being performed simultaneously.

Poly-Branched Poly-Olefin Structures

A key element of the process of the present invention is the feedstock poly-branched poly-olefins. The better to illustrate the possible complexity of the preferred poly-branched poly-olefin feedstocks for the invention, structures (a) to (j) below are shown. These are only a few of hundreds of possible preferred structures that make up the potential feedstocks, and should not be taken as limiting the invention.

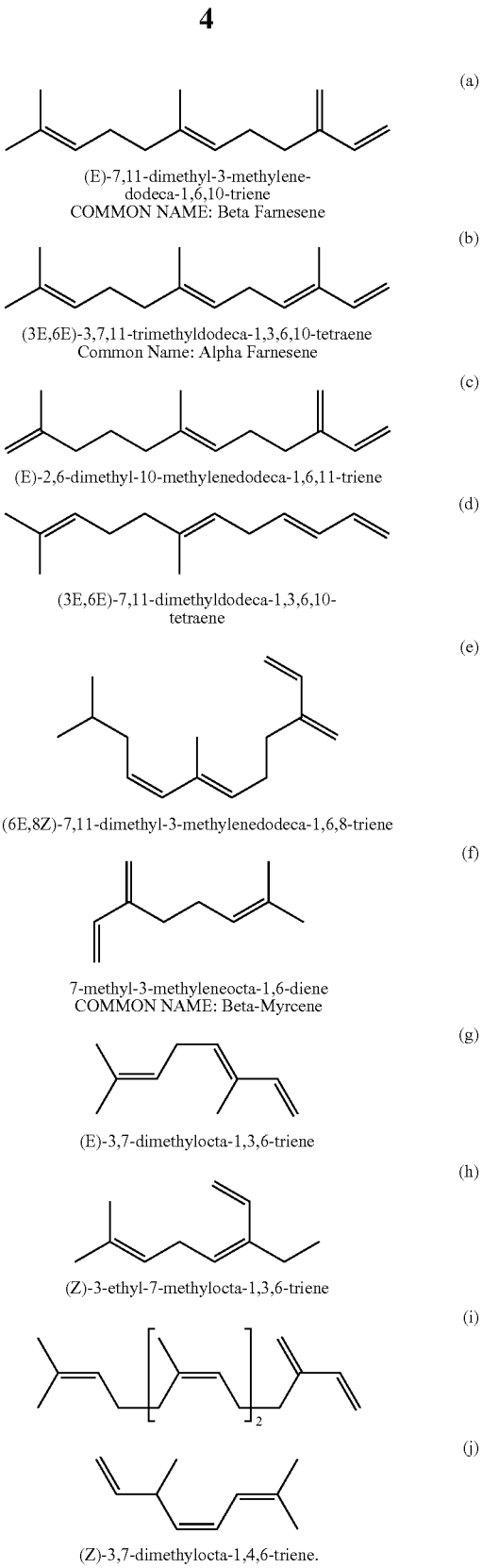

(a) (E)-7,11-dimethyl-3-methylene-dodeca-1,6,10-triene
COMMON NAME: Beta Farnesene (b) (3E,6E)-3,7,11-trimethyldodeca-1,3,6,10-tetraene
Common Name: Alpha Farnesene (c) (E)-2,6-dimethyl-10-methylenedodeca-1,6,11-triene (d) (3E,6E)-7,11-dimethyldodeca-1,3,6,10-tetraene (e) (6E,8Z)-7,11-dimethyl-3-methylenedodeca-1,6,8-triene (f) 7-methyl-3-methyleneocta-1,6-diene
COMMON NAME: Beta-Myrcene (g) (E)-3,7-dimethylocta-1,3,6-triene (h) (Z)-3-ethyl-7-methylocta-1,3,6-triene (i)

(j) (Z)-3,7-dimethylocta-1,4,6-triene.

The molecule represented by structure (d) can potentially come from a di-isoprene and is illustrative of the utility of the process to use other feedstocks than exclusively the described feedstock for the preferred inventions.

Compound (a), (b), (c) and (e) can be derived from:
i. natural derived farnesene extracted from pre-existing plants and organisms;
ii. farnesene obtained via genetically modified organisms;
iii. synthetically derived trimers of isoprene;
iv. mixtures thereof.

Other examples of illustrated poly-branched poly-olefins are shown to document the utility of the processes of the invention to function with other olefins which may not be derived from processes i, ii, iii, or iv. These examples are less preferred.

A highly preferred olefin of the invention is (k) which can be used to convert to the preferred alcohol 1 of the invention.

i. Naturally Derived Farnesene Extracted from Pre-Existing Plants and Organisms:

Examples of naturally derived farnesenes and potentially other structures illustrated can come from the class of natural materials called terpenes. Terpenes are a large and varied class of hydrocarbons, produced primarily by a wide variety of plants, particularly conifers and other pines, though also by some insects such as swallowtail butterflies. As many of these materials isolated from plants and other natural organisms often are present as gross mixtures, it may be desirable to purify the components before use in the processes of the invention. See U.S. Pat. No. 4,605,783.

The term "farnesene" refers to a set of six closely related chemical compounds which all are sesquiterpenes. α-Farnesene and β-farnesene are isomers, differing by the location of one double bond. α-Farnesene (structure (b) above) is 3,7,11-trimethyl-1,3,6,10-dodecatetraene and β-farnesene (structure (a) above) is 7,11-dimethyl-3-methylene-1,6,10-dodecatriene. The alpha form can exist as four stereoisomers that differ about the geometry of two of its three internal double bonds (the stereoisomers of the third internal double bond are identical). The beta isomer exists as two stereoisomers about the geometry of its central double bond.

Two of the α-farnesene stereoisomers are reported to occur in Nature. (E,E)-α-Farnesene is the most common isomer. It is found in the coating of apples, and other fruits. (Z,E)-α-Farnesene has been isolated from the oil of perilla.

β-Farnesene has one naturally occurring isomer. The E isomer is a constituent of various essential oils. Several plants, including potato species, have been shown to synthesize this isomer.

ii. Farnesene Obtained Via Genetically Modified Organisms:

Several recent examples now allow for farnesene and other isoprene derivatives to be supplied via genetically modified organisms. Examples of such sources can be found in U.S. Pat. No. 7,399,323 B2. This reference describes potential use of farnesane as fuel derived via genetically engineered farnesene. Another source of genetically engineered farnesene and isoprenes is disclosed in U.S. Pat. No. 6,872,556 B2.

iii. Synthetically Derived Trimers of Isoprene:

Synthetically derived trimers can be obtained from various sources, two of which are shown in Japaneses Patents JP 52031841 and JP 48040705. JP 48040705 teaches a process to make compound (b) as illustrated above. The process involves oligomerization of isoprene in the presence of divalent Ni, phosphine derivatives, and organomagnesium compounds to give high yields i.e. 75% of compound (b). Other synthetic processes to derive trimers are available.

Mixtures of any of the above disclosed non-limiting feedstocks can be used in the processes of the invention as well as isomeric forms.

Process for Preparing a Detergent Alcohol Mixture

A first process embodiment of the present invention is a process for preparing a detergent alcohol mixture comprising:
a. providing one or more poly-branched poly-olefins wherein the poly-branched poly-olefins must contain one non-branched terminal olefin and one or more additional branched olefins in the molecule;
b. hydroformylating said poly-branched poly-olefins to produce a poly-branched olefin containing aldehyde with one or more olefins or mixture thereof, utilizing a catalyst selected from the group IX transition metals modified or unmodified and process conditions comprising: a process temperature ranging from about 50° C. to about 130° C., a hydrogen to carbon monoxide mole ratio ranging from about 0.25 to 1 to about 4 to 1, a total pressure ranging from about 300 psig to about 2000 psig;
c. reducing the aldehyde product of step (b) in the presence of hydrogen and a hydrogenation catalyst, utilizing process conditions comprising: a process temperature ranging from about 20° C. to about 130° C., a hydrogen pressure ranging from 100 psig to about 2000 psig; and
d. removing said poly-branched alcohol composition from said catalyst.

This first process embodiment can be illustrated by the following PROCESS SCHEME I which uses, as a non-limiting example, alpha farnesene as feedstock.

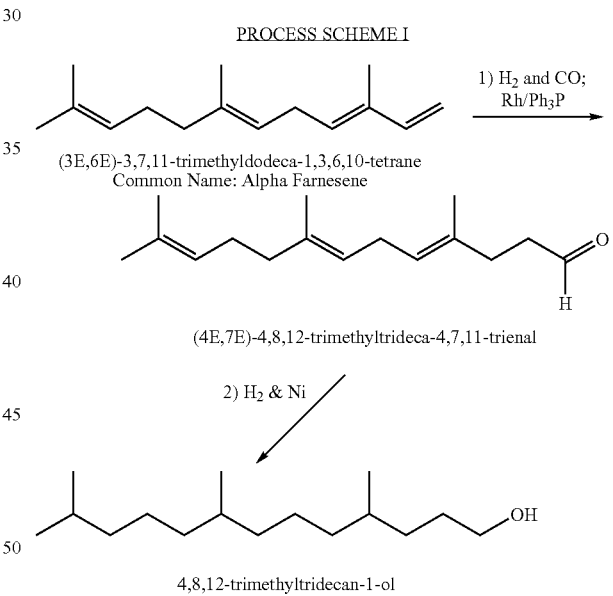

Selection of the olefin in process step a is previously illustrated above. Any mixture or single material can be used from the list of structures or others which have the elements of being poly-branched and poly-olefinic with one olefin not branched at a terminal position on the chain.

Step 1—Hydroformylation—The one or more poly-branched poly-olefins (alpha farnesene shown here) may be reacted in the presence of hydrogen, carbon monoxide, and a Rhodium/triphenyphosphine catalyst to give the desired poly-branched poly-olefinic aldehydes. Other Group IX metals can also be used in this process step such as Cobalt. Cobalt and Rhodium are preferred, but Iridium is also acceptable for the process. Carbonylhydridotris(triphenylphosphine)rhodium(I) is a metal complex which can be purchased from Aldrich Chemical and other sources, to be used along with triphenylphosphine. As some hydroformylation catalysts are pyrophoric it is advisable to use standard preparation methods and handling procedures to keep oxygen levels below 40 ppm, averaging below 1 ppm.

Agitation is obtained by using a PTFE coated magnetic stir bar placed in the glass liner of the 300 ml reactor. The reactor, in turn, is placed on a magnetic stir plate that is magnetically coupled to the stir bar. Agitation rates of up to 200 rpm are possible without losing the magnetic coupling.

Unmodified Rh may also be used but may need to used at higher temperatures and pressures due to lower selectivity HRh(CO)(PPh3)2 is a catalyst which provides good selectivity particularly if used in Step 1 at 25° C., 90-200 psig and with 1:1 ratio mixtures of carbon monoxide and hydrogen. Other catalysts such as HRh(CO)(PPh3)2 can also provide good selectivity if run at reaction conditions such as 80 to 100 psig and 90° C. with 1:1 ration mixtures of carbon monoxide and hydrogen and high ratios of excess triphenyphosine at around 800:1 relative to the Rhodium. The use of rhodium with excess phosphine ligand creates an active, selective, and stable catalyst system at 80-100 psig and 90° C.

Temperature, pressure and the ratio of carbon monoxide to hydrogen are needed to control the reaction to provide a mono aldehyde in process step b of the present process invention (PROCESS SCHEME 1, Step 2). Temperatures ranging from 60 to 90° C. with pressures of from 300 to 600 psig and ratios of carbon monoxide to hydrogen to carbon monoxide of 2:1 may be used. As noted above modified Rhodium is preferred however if one desires to use unmodified catalyst for process step b one should use Cobalt instead with it's higher reaction and ability to isomerize olefins to give more of the desired terminal addition product. One should also use higher ratios of hydrogen as well with Cobalt to avoid internal hydroformylation producing less desired products outside the scope of this invention.

Polyaldehyde formation may be encouraged to occur by operating the process at a temperatures above 90° C. Higher ratios of carbon monoxide to hydrogen may also be used to maximize dialdehydes and other polyaldehydes.

Step 2—Reduction—In step 2, the produced poly-branched poly-olefinic aldehydes are reacted with hydrogen in the presence of a reduction catalyst, such as nickel, to provide a substantially trimethyl substituted saturated alcohol. Nickel on Kieselguhr is one non-limiting example of reduction catalyst system. Rhodium on Silica, Palladium on Kieselguhr are other examples of catalysts which can be used for the reduction of the poly-branched poly-olefinic aldehydes.

Process step c is carried out with a variety of catalysts ranging from Nickel on Kieselguhr Rhodium on Silica, Palladium on Kieselguhr are other examples of catalysts which can be used for the reduction of the poly-branched poly-olefinic aldehydes. Reaction conditions vary from 20° C. to about 130° C., a hydrogen pressure ranging from 100 psig to about 2000 psig of hydrogen and catalyst loadings can typically be in range of from 1 to 5% on the substrate relative to the poly-branched poly-olefinic aldehyde. Thus, a highly efficient process is defined providing a specific surfactant alcohol and alcohol mixtures for use in preparation of surfactants. Reaction times will vary according to catalyst ratio, temperature chosen and hydrogen pressure. Typical conditions are 150° C. at 1000 psig for 16 hours in batch mode. The process is not limited to batch processes. Continuous reaction can also be applied to the present invention. Formation of paraffin may be observed during the sequence of processes but is readily removed by distillation from the poly-branched poly-olefinic aldehyde after process step c or may be also removed from the poly-branched alcohol after performing process step d if necessary. Thus, a highly efficient process is defined to provide a specific surfactant alcohol and alcohol mixtures for use in preparation of surfactants. The polybranched alcohol compositions can be converted by a number of conventional means to the surfactant compositions such as the detergent alcohol ethoxylate, the detergent alcohol sulfate and detergent alcohol ethoxylated sulfate which exemplified in the synthesis examples.

SYNTHESIS EXAMPLE I

Using Process Scheme I

Synthesis of Farnesene Derived Poly-Branched Poly-Olefin Containing Aldehyde and Mixtures Thereof 1.6 grams of Carbonylhydridotris(triphenylphosphine) rhodium(I) [17185-29-4], 3.0 grams of Triphenylphosphine [603-35-0], and 336 grams of a mixture of isomers of alpha-farnesene [502-61-4] are charged to a 600 mL stainless steel stirred pressure vessel. The reactor is purged of air using vacuum and nitrogen cycles then charged with a 2:1 ratio mixture of carbon monoxide and hydrogen to an initial pressure of 300 psig. The reactor is heated to 85° C. with agitation with a magnetic stir bar at 500 rpm and the pressure is adjusted to 600 psig using a 2:1 ratio mixture of carbon monoxide and hydrogen. As carbon monoxide and hydrogen are consumed by the reaction, the pressure is maintained by using a 1:1 ratio mixture of carbon monoxide and hydrogen. The contents of the reactor are sampled with time and analyzed by gas chromatography ("GC") to monitor the progress of the reaction. When the GC sample analysis indicates that the starting alpha-farnesene is completely consumed, the reaction mixture is cooled to room temperature and the carbon monoxide:hydrogen mixture is vented. Depending on the purity of the alpha-farnesese, process time can run between several hours to as long as 70 hours. Before proceeding to the next step of the reaction, residual carbon monoxide is removed by using vacuum and nitrogen cycles. The aldehyde mixture is not removed from the reactor prior to conversion to alcohol in EXAMPLE II, although the Aldehyde could be purified if so desired or used in other reactions.

SYNTHESIS EXAMPLE II

Using Process Scheme I Steps c, d

Synthesis of Farnesene Derived Poly-branched Alcohol and Mixtures Thereof 20 grams of Nickel on Kieselguhr (60-weight % loading) and 200 mL of tetrahydrofuran are charged to a 600 mL stainless steel stirred pressure vessel. The reactor is purged of air using vacuum and nitrogen cycles then charged with hydrogen to an initial pressure about 600 psig. The mixture is heated to about 150° C. with stirring at 500 rpm. Hydrogen is charged to a final pressure of about 1000 psig and maintained at this pressure for 16 hours. The contents of the reactor are then cooled to room temperature and the pressure is reduced to about 50 psig.

The mixture obtained from SYNTHESIS EXAMPLE I is then charged to the reactor while excluding the introduction of air from the atmosphere while continuously stirring the reactor contents. The hydroformylation catalyst from SYNTHESIS EXAMPLE 1 may remain with the aldehyde mixture or may be removed from the aldehyde mixture prior to use. The reactor is then pressurized with hydrogen to an initial pressure of about 600 psig and heated to about 125° C. while agitating at about 500 rpm with a magnetic stir bar. Hydrogen pressure is then raised to 1000 psig and maintained at this pressure. The progress of the reaction is monitored by GC until additional product is no longer formed. The reaction time will vary according to the reaction conditions.

Purification of the crude alcohol mixture can be achieved by standard known procedures such as distillation or other purification methods known in the art.

SYNTHESIS EXAMPLE III

Using Process Scheme I

Synthesis of a Farnesene Derived mixture Primarily Consisting of 4,8,12-Trimethyl-tridecan-1-ol (Alcohol 1) and 3-Ethyl-7,11-dimethyl-dodecan-1-ol (Alcohol 2) and Mixtures Thereof A 600 mL stainless steel stirred pressure vessel with magnetic stir bar agitation issued as Reactor #1, using vacuum to draw in the materials while avoiding air. 1.80 grams of Carbonylhydridotris(triphenylphosphine) rhodium(I) [17185-29-4] and 5.84 grams of Xantphos [161265-03-8] were slurried in 77 grams of pentane and charged to Reactor #1. The pentane is removed using vacuum and no heat, then 50 mls of toluene are added. The reactor is purged of air using vacuum and nitrogen cycles then charged with 10 atm of a 1:1 ratio mixture of carbon monoxide and hydrogen, and heated to 60° C. for two hours and then cooled to 30° C.

The reactor is placed under vacuum then 100.86 grams of trans-beta-Farnesene [18794-84-8] plus 50 mls of toluene are charged to the reactor while excluding air. The reactor is purged of air using vacuum and nitrogen cycles and then charged with about 44 atm of a 2:1 ratio mixture of carbon monoxide and hydrogen. The reactor is initially heated to 45° C. and kept at that temperature for 19 hours. As carbon monoxide and hydrogen are consumed by the reaction, the pressure is maintained by using a 1:1 ratio mixture of carbon monoxide and hydrogen.

The contents of the reactor are sampled with time and analyzed by GC to monitor the progress of the reaction. After 19 hours the reaction temperature is increased to 85° C. while continuing the reaction for an additional 54 hours while maintaining the pressure. Before proceeding to the next step of the reaction, residual carbon monoxide is removed by using heat and vacuum. At the same time, toluene is evaporated to less than 15% as determined by GC analysis.

A 600 mL stainless steel stirred pressure vessel is used as reactor #2. Nickel on Silica (10 grams of 64% Nickel on silica, reduced and stabilized) slurried in 50 mls of pentane is charged to Reactor #2 followed by an additional 50 mls of pentane to rinse the lines. The pentane is evaporated off using heat and vacuum. The reactor is heated to between 270 and 275° C. while under vacuum then charged with hydrogen to 150-250 psig H2 through the bottom drain port to keep that area clear of catalyst and to prevent clogging of the drain port. The reactor is allowed to stand for 15 minutes. The hydrogen is vented and the reactor is then placed under vacuum using a water aspirator. The reactor is charged with hydrogen a second time, left for 15 minutes, then vented, and then vacuum is applied. This is repeated two more times. The reactor is then charged with hydrogen to about 250 psig (always through the bottom drain port) and the reactor is allowed to stand overnight at temp (270-275° C.) and pressure (about 250 psig H2). The reactor is then vented, vacuum applied for 15 minutes, then recharged with hydrogen (150-250 psig) for 15 minutes. This is repeated 2 more times. The reactor was charged with hydrogen to 250 psig then cooled to less than 40° C.

The drain line of Reactor #1 is connected to Reactor #2. The contents of Reactor #1 is charged to Reactor #2 while excluding air, by pressurizing Reactor #1 with hydrogen and pushing the liquid from Reactor #1 into Reactor #2 while keeping the reactor agitation at about 200 RPM. Additional hydrogen is charged to the reactor through the bottom drain port to clear the area of catalyst. The reactor is then charged with hydrogen to 150 psig (always through the bottom drain port) and the reactor was stirred at about 500 RPM. The reaction is continued until hydrogen consumption ceases and samples drained from the reactor indicate that the reaction is complete. The reactor is heated for 24 Hours at 125° C. while keeping the hydrogen pressure between 450 and 500 psig H2. The product mix is drained from the reactor. The catalyst is removed by filtration and volatile materials are removed using a rotary evaporator. The analysis of the final mixture by gas chromatography indicated that the mixture contains about 39% 4,8,12-trimethyl-tridecan-1-ol, 34% 3-ethyl-7,11-dimethyl-dodecan-1-ol, 10% total paraffin and mixed olefins, and 10% total mixed di-oxygenated materials.

SYNTHESIS EXAMPLE IV

Using Process Scheme I Steps a, b

Synthesis of Beta-Myrcene ($C_{11}$) Derived Poly-Branched Poly-Olefin Containing Aldehyde and Mixtures Thereof 1.6 grams of Carbonylhydridotris(triphenylphosphine) rhodium(I) [17185-29-4], 3.0 grams of Triphenylphosphine [603-35-0], and 336 grams of beta-myrcnen [84776-26-1], a mixture of isomers are charged to a 600 mL stainless steel stirred pressure vessel. The reactor is purged of air using vacuum and nitrogen cycles then charged with a 2:1 ratio mixture of carbon monoxide and hydrogen to an initial pressure of 300 psig. The reactor is heated to 85° C. with stirbar agitation at 500 rpm and the pressure adjusted to 600 psig using the 2:1 ratio mixture of carbon monoxide and hydrogen. As carbon monoxide and hydrogen are consumed by the reaction, the pressure is maintained by using a 1:1 ratio mixture of carbon monoxide and hydrogen. The contents of the reactor are sampled with time and analyzed by GC to monitor the progress of the reaction. When the GC sample analysis indicates that the starting beta-myrcene is completely consumed, the reaction mixture is cooled to room temperature and the carbon monoxide:hydrogen mixture is vented. Depending on the purity of the beta-myrcene, the process time can vary. Before proceeding to the next step of the reaction, residual carbon monoxide is removed by using vacuum and nitrogen cycles. The aldehyde mixture is not removed from the reactor prior to conversion to alcohol in EXAMPLE V, although the aldehyde could be purified if so desired or used in other reactions.

SYNTHESIS EXAMPLE V

Using Process Scheme I Steps c, d

Synthesis of beta-Myrcene Derived Poly-branched Alcohol and Mixtures Thereof

Nickel on Kieselguhr (20 grams of 60-weight % loading) plus tetrahydrofuran (200 mL) are charged to a 600 mL stainless steel stirred pressure vessel. The reactor is purged of air using vacuum and nitrogen cycles then charged with hydrogen to an initial pressure about 600 psig. The mixture is heated to about 150° C. with stirring at 500 rpm. Hydrogen is charged to a final pressure of about 1000 psig and maintained at this pressure for 16 hours. The contents of the reactor are then cooled to room temperature and the pressure is reduced to about 50 psig.

The aldehyde mixture obtained from SYNTHESIS EXAMPLE IV is then charged to the reactor while excluding the introduction of air from the atmosphere while continuously stirring the reactor contents. The hydroformylation catalyst remains with the aldehyde mixture. If so desired the catalyst may be removed from the aldehyde mixture prior to use. The mixture is then pressurized with hydrogen at an initial pressure of about 600 psig and heated to about 125° C. while agitating at about 500 rpm. Hydrogen pressure is then raised to 1000 psig and maintained at this pressure while periodically sampling the reactor contents for analysis by GC. The progress of the reaction is monitored by GC until additional product is no longer formed. The reaction time will vary according to the reaction conditions. Purification of the crude alcohol mixture can be achieved by standard known procedures such as distillation or other purification methods known in the art.

SYNTHESIS EXAMPLE VI

Using Process Scheme I

Synthesis of a beta-Myrcene Derived mixture Primarily Consisting of 4,8-dimethyl-nona-1-ol and 3-Ethyl-7-methyl-octa-1-ol and Mixtures Thereof 1.80 grams of Carbonylhydridotris(triphenylphosphine) rhodium(I) [17185-29-4] and 5.84 grams of Xantphos [161265-03-8] slurried in 77 grams of pentane are charged to Reactor #1, a 600 mL stainless steel stirred pressure vessel having stirbar agitation of 300-500 rpm used throughout, using vacuum to draw in the materials while avoiding air. The pentane is removed using vacuum and no heat. 50 mls of toluene is added. The reactor is purged of air using vacuum and nitrogen cycles then charged with 10 atm of a 1:1 ratio mixture of carbon monoxide and hydrogen. It is heated to 60° C. for two hours and then cooled to 30° C. The reactor is placed under vacuum. 100.86 grams of beta-Myrcene [18794-84-8] plus 50 mls of toluene are charged to the reactor while excluding air. The reactor is purged of air using vacuum and nitrogen cycles then charged with about 44 atm of a 2:1 ratio mixture of carbon monoxide and hydrogen. The reactor is initially heated to 45° C. and kept at that temperature for 19 hours. As carbon monoxide and hydrogen are consumed by the reaction, the pressure is maintained by using a 1:1 ratio mixture of carbon monoxide and hydrogen.

The contents of the reactor are sampled with time and analyzed by GC to monitor the progress of the reaction. After 19 hours the reaction temperature is increased to 85° C. while continuing the reaction for an additional 54 hours while maintaining the pressure.

Before proceeding to the next step of the reaction, residual carbon monoxide is removed by using heat and vacuum. At the same time, toluene is evaporated to less than 15% by GC analysis.

Nickel on Silica (10 grams of 64% Nickel on silica, reduced and stabilized) slurried in 50 mls of pentane is charged to a 600 mL stainless steel stirred pressure vessel followed by an additional 50 mls of pentane to rinse the lines. The pentane is evaporated off using heat and vacuum. The reactor is heated to between 270 and 275° C. while under vacuum, and then charged with hydrogen to between 150 and 250 psig hydrogen through the bottom drain port to keep that area clear of catalyst and to prevent clogging of the drain port. The reactor is allowed to stand for 15 minutes. The hydrogen is vented and the reactor is then placed under vacuum using a water aspirator. The reactor is charged with hydrogen, left for 15 minutes, then vented, then vacuum was applied. This is repeated two more times. The reactor is then charged with hydrogen to about 250 psig (always through the bottom drain port) and the reactor is allowed to stand overnight at temp (270-275° C.) and pressure (about 250 psig H2).

The reactor is vented and vacuum is applied for 15 minute. Then the reactor is recharged with hydrogen (150-250 psig) for 15 minutes. This is repeated 2 more times. The reactor is charged with hydrogen to 250 psig then cooled to <40° C.

The drain line of Reactor #1 is connected to Reactor #2. The contents of Reactor #1 is charged to Reactor #2 while excluding air, by pressurizing Reactor #1 with hydrogen and pushing the liquid from Reactor #1 into Reactor #2 while keeping the reactor agitation at about 200 rpm. Additional hydrogen is charged to the reactor through the bottom drain port to clear the area of catalyst. The reactor is then charged with hydrogen to 150 psig (always through the bottom drain port) and the reactor is stirred at about 500 rpm. The reaction is continued until hydrogen consumption ceases and samples drained from the reactor indicate that the reaction is complete. The product mix is drained from the reactor, the catalyst is removed by filtration, and volatile materials are removed using a rotary evaporator.

A second process embodiment represented by PROCESS SCHEME II includes the step of selectively hydrogenating the poly-branched polyolefin before the hydroformylation.

PROCESS SCHEME II

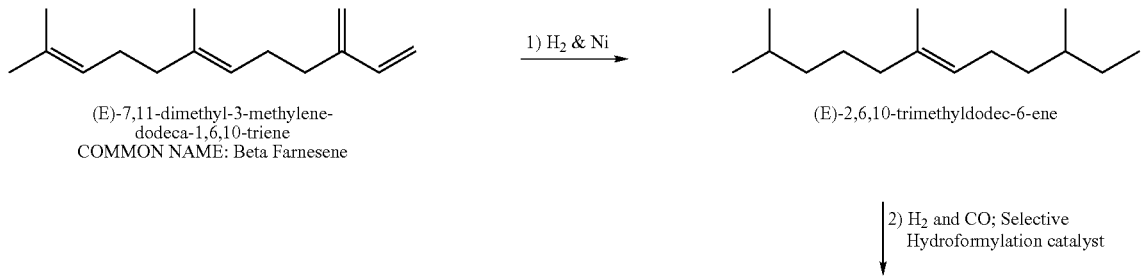

(E)-7,11-dimethyl-3-methylene-dodeca-1,6,10-triene
COMMON NAME: Beta Farnesene

1) H$_2$ & Ni (E)-2,6,10-trimethyldodec-6-ene

2) H$_2$ and CO; Selective Hydroformylation catalyst

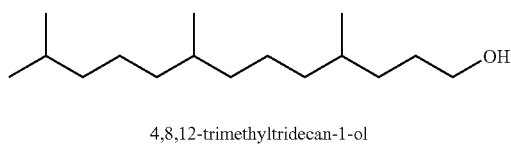

4,8,12-trimethyltridecan-1-ol $\xleftarrow{\text{3) H}_2 \text{ \& Ni}}$

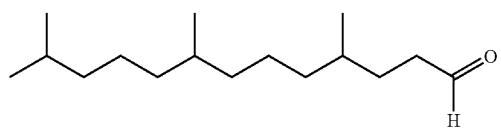

4,8,12-trimethyltridecanal

Accordingly the embodiment comprises:
a. providing a poly-branched poly-olefins to a reactor;
b. selectively hydrogenating all but one olefin of the poly-branched poly-olefin mixture producing a poly-branched mono-olefin mixture;
c. Hydroformylating the poly-branched mono-olefin mixture product of step (b) in the presence of a selective hydroformylation catalyst and process conditions comprising: a process temperature ranging from about 50° C. to about 130° C., a hydrogen to carbon monoxide mole ratio ranging from about 0.25 to 1 to about 5 to 1, a total pressure ranging from about 300 psig to about 2000 psig; producing a poly-branched aldehyde mixture;
d. reducing the poly-branched aldehyde product of step (c) in the presence of hydrogen and a metal catalyst; and
e. removing said poly-branched alcohol composition from said catalyst.

In some cases, step d of this embodiment can be minimized or even eliminated since some hydroformylation catalysts can convert the mono olefin directly to the alcohol with only minor amounts of aldehyde intermediate. With this equivalent process there may still be a need to use step d as a polishing step to convert the minor amount of aldehyde to alcohol since this aldehyde may be deleterious to reactions involving conversion to surfactants. Examples of such catalysts are described in U.S. Pat. No. 3,420,898.

If polybranched mono-olefins from other biological or synthetic means, reaction steps a and b can be skipped and steps c and d performed directly.

Selective Hydrogenation—Catalysts and systems which can be used for process step b of PROCESS SCHEME II to give selective hydrogenation to mono olefins are described in U.S. Pat. No. 6,627,778 B2 by Xu et al. It describes specific catalysts and reaction conditions to convert diolefins to mono olefins. This process can be applied to the poly-branched poly-olefin reaction sequence in this process embodiment. Other suitable catalysts and systems are described in U.S. Pat. Nos. 4,695,560, 4,523,048, 4,520,214, 4,761,509 and Chinese Patent CN 1032157. Some embodiments of the catalyst in this process may be characterized in that it contains 1.0 to 25 wt % of nickel, 0.05 to 1.5 wt % of sulfur and the support is small $Al_2O_3$ balls made by the oil-drop method, which balls have a pore volume of from 1.44 to 3.0 cm$^3$/g, a surface area larger than 150 m$^2$/g and have no precious metals, and essentially have no halogens, alkali earth metals and alkali metals (<0.1 wt %). Because the main active element of the catalyst used in this process is nickel, selective hydrogenation has to be conducted at a temperature higher than 200° C. to attain a certain activity. In addition, in order to increase the selectivity of diolefins, to mono-olefins, it is necessary to frequently sulfurize the catalyst so as to suppress its activity.

Another approach to providing an intermediate mono olefin, if it so desired, from step b of this process embodiment is to not control the hydrogenation, but use standard hydrogenation catalysts and allow for formation of a mixture of mono olefin and paraffin. The reaction mixture can then be carried through the process sequence of hydroformylation c and reduction d and paraffin can be removed from the final branched alcohol after process d by standard distillation.

For this process embodiment step c, hydroformylation, temperature, pressure and ratio of hydrogen to carbon monoxide are needed to control the reaction to minimize paraffin formation in this case. Preferred temperatures range from 60 to 90° C. with pressures of from 300 to 600 psig and higher ratios of carbon monoxide mixture of 2:1 or higher being preferred or lower to minimize hydrogenation of the olefins to paraffins. As noted above modified Cobalt is preferred with it's higher reactivity and ability to isomerize olefins to give more of the desired terminal addition product. If one desires to use unmodified Cobalt, lower ratios of hydrogen as well should be used to avoid internal hydroformylation producing less desired products outside the scope of this invention.

Process step d is carried out with a variety of catalysts ranging from Nickel on Kieselguhr Rhodium on Silica, Palladium on Kieselguhr are other examples of catalysts which can be used for the reduction of the poly-branched aldehydes. Reaction conditions vary from 20° C. to about 130° C., a hydrogen pressure ranging from 100 psig to about 2000 psig of hydrogen and catalyst loadings can typically be in range of from 1 to 5% on the substrate relative to the poly-branched poly olefinic aldehyde. Thus, a highly efficient process is defined providing a specific surfactant alcohol and alcohol mixtures for use in preparation of surfactants. Reaction times will vary according to catalyst ratio, temperature chosen and hydrogen pressure. Typical conditions are 150° C. at 1000 psig for 16 hours in batch mode. The process is not limited to batch reactions, but continuous reaction can also be applied to the invention. Formation of paraffin may be observed during the sequence of processes but is readily removed by distillation from the poly-branched polyolefinic alcohol after process step d or may be also removed from the poly-branched alcohol after performing process step e if necessary.

SYNTHESIS EXAMPLE VII

Process Scheme II

Synthesis of Farnesene Derived Poly-Branched Mono-Olefin and Mixtures Thereof

Nickel on Silica catalyst (5 grams of 64% Nickel on silica, reduced and stabilized) is slurried in 50 mls of pentane and charged to a 600 mL stainless steel stirred pressure vessel followed by an additional 50 mls of pentane to rinse the lines. The pentane is evaporated off using heat and vacuum. The reactor is heated to between 270 and 275° C. while under vacuum then charged with hydrogen to between 150 and 250 psig hydrogen through the bottom drain port to keep that area clear of catalyst and to prevent clogging of the drain port. The reactor is allowed to stand for 15 minutes. The hydrogen is vented, and the reactor is then placed under vacuum using a water aspirator. The reactor is charged with hydrogen, left for 15 minutes, then vented, and vacuum applied. This is repeated two more times. The reactor is then charged with hydrogen to about 250 psig (always through the bottom drain port) and the reactor is allowed to stand overnight at temp (270-275° C.) and pressure (about 250 psig H2). The reactor is then vented, vacuum is applied to the reactor for 15 minutes, and the reactor is recharged with hydrogen (150-250 psig) for 15 minutes. This is repeated 2 more times. The reactor is charged with hydrogen to 250 psig then cooled to <40° C.

Trans-beta-farnesene [18794-84-8] (100 grams) is charged to a 300 ml sample cylinder followed by 50 mls of pentane to chase the lines. The sample cylinder is connected to the 600 ml reactor with tubing and valving. The sample cylinder is purged of atmosphere using vacuum-hydrogen cycles. Hydrogen is introduced through the bottom of the sample cylinder and through the liquid mixture to help sparge the liquid to assist in removing low levels of air. A total of four vacuum-hydrogen cycles are completed. The trans-beta-farnesene mixture is then charged to the 600 ml reactor, while excluding air, by pressurizing the sample cylinder with hydrogen and pushing the liquid into the reactor with the reactor agitation at about 200 rpm. Additional hydrogen is charged to the reactor through the bottom drain port to clear the area of catalyst. The reactor is then charged with hydrogen to 150 psig (always through the bottom drain port) and the reactor is stirred at about 500 rpm. The reaction is continued until hydrogen consumption ceases and samples drained from the reactor indicate that the reaction is complete. The product-pentane mix is drained from the reactor. The catalyst is removed by filtration, and the pentane is removed using a rotary evaporator.

SYNTHESIS EXAMPLE VIII

Process Scheme II Using Product of Example VII

Synthesis of Farnesene Derived Poly-Branched Alcohols, and Mixtures Thereof 1.17 mmol of Dicobalt Octacarbonyl and 4.7 mmol of Eicosyl Phobane (a mixture of isomers [13887-00-8] and [13886-99-2]) are combined in 48 mls of dried, degassed 2-propyl alcohol in a 300 mL stainless steel pressure vessel that has a glass liner and PTFE coated stir bar. 47.7 mmol of the farnesene-derived paraffin/mono-olefin mixture obtained in SYNTHESIS EXAMPLE VII, previously dried over X Å molecular sieves and filtered, is added to the feed tube of the reactor. The reactor lines are purged of air using vacuum and nitrogen cycles. The 300 ml reactor is then purged with a 1:1 ratio mixture of carbon monoxide and hydrogen.

The reactor containing the mixture of Dicobalt Octacarbonyl, Eicosyl Phobane, and 2-propyl alcohol is charged to an initial pressure of about 150 psig with the 1:1 ratio mixture of carbon monoxide and hydrogen. The reactor is heated to from 60 to 65° C. with stirbar agitation at 150 to 200 rpm with the pressure kept between 150 and 200 psig using a 1:1 ratio mixture of carbon monoxide and hydrogen. After 1 to 2 hours the reactor is cooled to below 40° C.

The reactor is vented and the Farnesene-derived paraffin/mono-olefin mixture is charged to the reactor. The reactor is then charged with a 1:2 ratio mixture of carbon monoxide and hydrogen. The reactor is then heated to between 160 and 165° C. while keeping the pressure between 500 and 700 psig using the 1:2 ratio CO:H2 gas mixture. The contents of the reactor are sampled with time and analyzed by GC to monitor the progress of the reaction. When the GC sample analysis indicates that the reaction is complete, the reaction mixture is cooled to room temperature and the carbon monoxide-hydrogen mixture is vented.

Alcohol product may be formed directly by this catalyst and only a polishing step of hydrogenation is needed to provide stable product alcohols.

SYNTHESIS EXAMPLE IX

Using Process Scheme II Step c Via Purchased Terminal Mono Olefin of Farnesene

Synthesis of 4,8,12-Trimethyl-tridecanal and Mixtures Thereof 1.22 grams of Carbonylhydridotris(triphenylphosphine)rhodium(I) [17185-29-4] and 3.11 grams of Xantphos [161265-03-8] slurried in 53 grams of hexanes are charged to a 600 mL stainless steel stirred pressure vessel with stribar agitation of about 300 to 500 rpm, using vacuum to draw in the samples while avoiding air. The reactor is purged of air using vacuum and nitrogen cycles, then charged with 10 atm of a 1:1 ratio mixture of carbon monoxide and hydrogen and heated to 60° C. for two hours, and then cooled to 30° C. The reactor is placed under vacuum. 27.4 grams of 3,7,11-Trimethyl-1-dodecene [1189-36-2] plus 85 grams of toluene are charged to the reactor while excluding air. The reactor is purged of air using vacuum and nitrogen cycles, then charged with 10 to 15 atm of a 2:1 ratio mixture of carbon monoxide and hydrogen. The reactor is heated to 45° C. As carbon monoxide and hydrogen are consumed by the reaction, the pressure was maintained by using a 1:1 ratio mixture of carbon monoxide and hydrogen. The contents of the reactor are sampled with time and analyzed by GC to monitor the progress of the reaction. When the GC sample analysis indicates that the reaction is complete, the reaction mixture is cooled to room temperature and the carbon monoxide:hydrogen mixture is vented.

Depending on the purity of the 3,7,11-Trimethyl-1-dodecene, process time can run between several hours to as long as 120 hours. Before proceeding to the next step of the reaction, residual carbon monoxide is removed by using vacuum and nitrogen cycles. The aldehyde mixture does not have to be removed from the reactor prior to conversion to alcohol in EXAMPLE IX, although the Aldehyde could be purified if so desired or used in other reactions.

SYNTHESIS EXAMPLE X

Using Process Scheme II Step d

Synthesis of 4,8,12-Trimethyl-tridecan-1-ol and Mixtures Thereof

Nickel on Kieselguhr (20 grams of 60-weight % loading) plus tetrahydrofuran (200 mL) are charged to a 600 mL stainless steel stirred pressure vessel. The reactor is purged of air using vacuum and nitrogen cycles then charged with hydrogen to an initial pressure of about 600 psig. The mixture is heated to about 150° C. with stirring at about 500 rpm. Hydrogen is charged to a final pressure of about 900 psig and maintained at this pressure for 16 hours. The contents of the reactor are then cooled to room temperature and the pressure reduced to about 50 psig.

The aldehyde mixture obtained from SYNTHESIS EXAMPLE VI is then charged to the reactor while excluding the introduction of air from the atmosphere while continuously stirring the reactor contents. The hydroformylation catalyst may remain with the aldehyde mixture. If so desired, the catalyst may be removed from the mixture prior to use. The mixture is then pressurized with hydrogen at an initial pressure of about 600 psig and heated to about 125° C. while agitating at about 500 rpm. Hydrogen pressure is then raised to about 900 psig and maintained at this pressure while periodically sampling the reactor contents for analysis by GC. The progress of the reaction is monitored by GC until additional product is no longer formed. The reaction time will vary according to the reaction conditions.

Purification of the crude alcohol mixture can be achieved by standard known procedures such as distillation or other purification methods known in the art.

Another embodiment of the process of the present invention is illustrated by PROCESS SCHEME III:

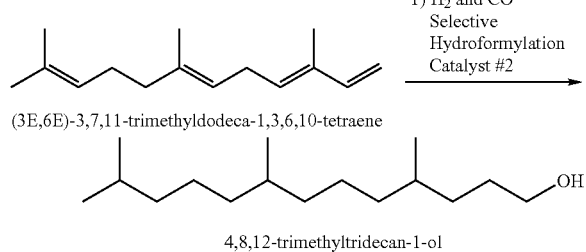

This embodiment is a process according to the first embodiment where, however, the hydroformylation and the reduction steps are performed simultaneously in a single step. Accordingly the process comprises:
  a. providing poly-branched poly-olefins wherein the poly-branched poly-olefins must contain one non-branched terminal olefin and one or more additional branched olefins in the molecule; and
  b. hydroformylating and reducing said poly-branched poly-olefin utilizing a catalyst selected from specific modified group IX transition metals and process conditions comprising: a process temperature ranging from about 90° C. to about 200° C., a hydrogen to carbon monoxide mole ratio ranging from about 2 to 1 to about 5 to 1, a total pressure ranging from about 300 psig to about 2000 psig; and
  c. removing said alcohol composition from said catalyst.

In the sequences of the third process embodiment above, the selection of the feedstocks for a is same as for the other embodiments. In the case of reaction step b a specialized hydroformylation catalyst is required and process conditions to afford maximum formation of the alcohol without isolation of the aldehyde. Furthermore, a key result of this process is also simultaneous hydrogenation of the unreacted olefins in the poly-branched poly-olefin feedstock. This is the most efficient process. However it is challenging to avoid formation of large amounts of paraffins. Catalysts of the type illustrated in U.S. Pat. No. 3,420,898 are suitable catalysts for this third embodiment. Process conditions for step b require a temperature ranging from about 50° C. to about 130° C., a hydrogen to carbon monoxide mole ratio ranging from about 2:1 to about 5:1, and a total pressure ranging from about 300 psig to about 2000 psig.

Catalysts preferred for this process are Cobalt based and modified with triphenylphosphine. Addition of small amounts of $Ph_2PCH_2CH_2CH_2CH_2PPh_2$ can aid this reaction.

Finally, step c is performed to remove the branched alcohol composition from the catalyst by distillation or other means commonly used in industry. Paraffins are formed more readily in this process and as such distillation is required to purify the alcohol.

SYNTHESIS EXAMPLE XI

Process Scheme III

Synthesis of Farnesene Derived Poly-Branched Alcohols, and Mixtures Thereof

In a facility for operating pressurized equipment 1.17 mmol of Dicobalt Octacarbonyl and 4.7 mmol of Eicosyl Phobane (a mixture of isomers [13887-00-8] and [13886-99-2]) are combined in 48 mls of dried, degassed 2-propyl alcohol in a 300 mL stainless steel pressure vessel that has a glass liner and PTFE coated stir bar. 47.7 mmol of trans-beta farnesene (previously dried over X Åmolecular sieves and filtered) are added to the feed tube attached to the reactor. The reactor lines are purged of air using vacuum and nitrogen cycles. The 300 ml reactor is then purged with a 1:1 ratio mixture of carbon monoxide and hydrogen.

The 300 ml reactor containing the mixture of Dicobalt Octacarbonyl, Eicosyl Phobane, and 2-propyl alcohol was charged to an initial pressure of about 150 psig with the 1:1 ratio Carbon monoxide-hydrogen mixture. The reactor is heated to between about 60 and 65° C. with agitation at from 150 to 200 rpm and the pressure kept between 150 and 200 psig using the 1:1 mixture of carbon monoxide and hydrogen. After 1 to 2 hours the reactor is cooled to below 40° C.

The reactor is vented and the trans-beta-Farnesene is charged to the reactor. The feed tube is isolated from the reactor and the reactor then charged with a 1:2 ratio mixture of carbon monoxide and hydrogen. The 300 ml reactor is then heated to between 160 and 165° C. while keeping the pressure between 500 and 700 psig using a 1:2 ratio mixture of carbon monoxide and hydrogen. The contents of the reactor are sampled with time and analyzed by GC to monitor the progress of the reaction. When the GC sample analysis indicates that the reaction is complete the reaction mixture is cooled to room temperature and the carbon monoxide:hydrogen mixture is vented. The resulting crude product contains Alcohol 1 and Alcohol 2.

Poly-branched Acyclic Aldehydes

Another embodiment of the invention is the formation of new acyclic aldehydes having either 16 or 21 carbon atoms and comprising at least three branches and three or less carbon-carbon double bonds. These novel aldehydes may have application in flavors and fragrances. Examples of these acyclic aldehydes include, but are not limited to 3-ethyl-7,11-dimethyldodecanal; 2,3,7,11-tetramethyl-dodecanal; 7,11,-dimethyl-3-vinyldodeca-6,10-dienal; 8,12-dimethyltrideca-4,7,11-trienal. Other embodiments are acyclic aldehydes having one, two or three carbon-carbon double bonds where the branches are methyl, ethyl or both. Another embodiment is where the acyclic aldehyde is saturated and the branches are methyl, ethyl or both. The acyclic aldehydes may be blended with other materials to obtain a useful compositions.

Non-limiting examples of structures of the novel poly-branched poly-olefin containing aldehydes of the invention are shown below:

The four aldehydes shown below (a1-a4) are structures formed by the reaction of beta farnesene according to process embodiment one.

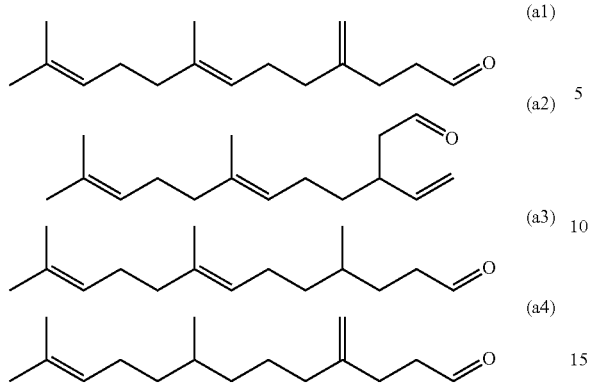

(a1)
(a2)
(a3)
(a4)

The below are also possible polybranched polyaldehyde structures which may be produced from beta farnesene by controlling the reaction conditions to maximize their production.

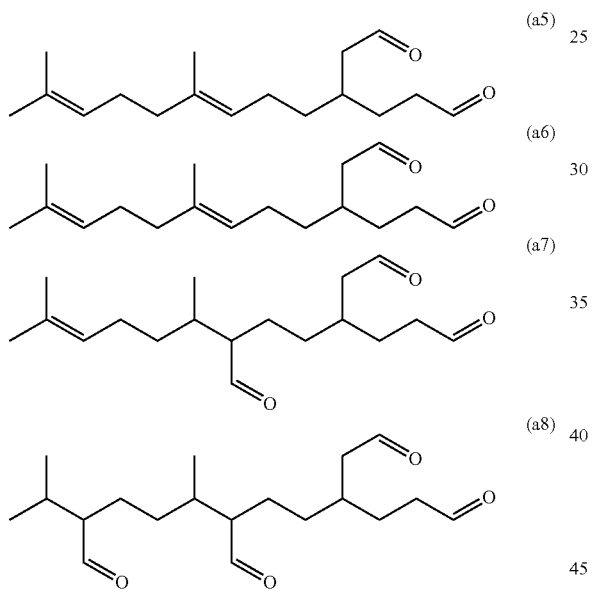

(a5)
(a6)
(a7)
(a8)

These structures represent preferred polybranched polyaldehydes having asymmetric structures wherein one of the aldehyde groups is on the terminal carbon of the longest carbon chain backbone of the molecule and at least one additional aldehyde group directly or indirectly attached to the molecule's backbone on the same side of the backbone's midpoint as the terminal aldehyde. Polyaldehydes are converted to polyalcohols and subsequently poly-functionalized surfactants. As with the polyaldehydes, preferred polyalcohols and subsequently poly-functionalized surfactants have one functional group attached to the terminal carbon of the longest carbon chain backbone of the molecule and at least one additional functional group directly or indirectly attached to the backbone on the same side of the backbone's midpoint as the terminal functional group. It is believed that the preferred poly-branched polysubstituted (e.g. di-anionic) surfactants have good soil suspending capacity without the tendency to crystallize and have poor solubility that linear di-anionic surfactants tend to demonstrate.

4,8,12-trimethyltridecanal (a9) is a possible aldehyde from process SCHEME II via the second process embodiment. (a10) is also another resulting aldehyde of the invention as well as mixtures of the two.

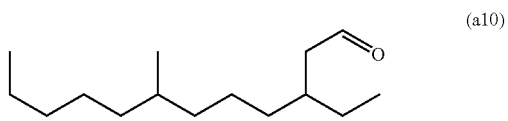

(a10)

The below (b1-b2) are poly-branched poly-olefin containing aldehyde which can be made from alpha farnesene. (b3) is the dialdehyde that may be produced under certain process conditions if production of the di aldehyde is desired.

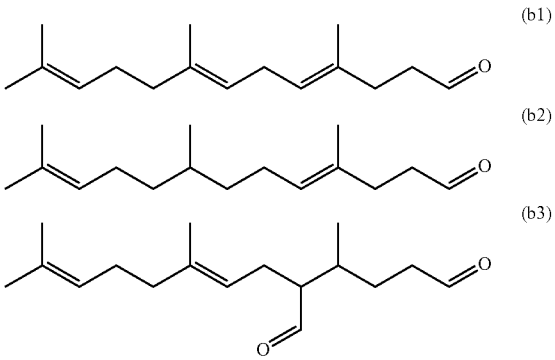

(b1)
(b2)
(b3)

The following ($C_{11}$ aldehydes 1-4) are also examples of aldehydes of the process invention according to PROCESS SCHEME I and detailed process elements in the chain lengths of $C_{11}$ and $C_{21}$. They can form from reaction according to process one using ocimene (1-2) and myrcene (3-4) with (aldehyde 5) coming from (Z)-3-ethyl-7-methylocta-1,3,6-triene. ($C_{11}$ poly-branched poly-olefin)

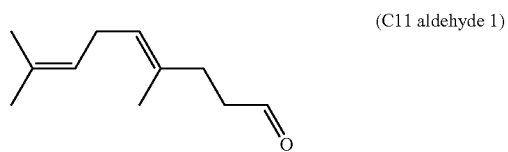

(C11 aldehyde 1)

(C11 aldehyde 2)

(C11 aldehyde 3)

(C11 aldehyde 4)

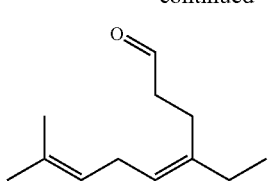
(C12 aldehyde 5)

The following is an example of a $C_{21}$ poly-branched poly-olefin aldehyde which can be derived from $C_{20}$ terpenes such as olefin (i).

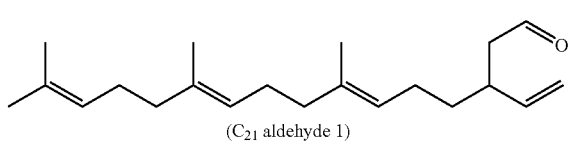
(C21 aldehyde 1)

Poly-branched Detergent Alcohols

Another embodiment of the present invention are the poly-branched detergent alcohols formed by the present process which contain 11, 16 or 21 carbon atoms.

Certain embodiments of the poly-branched detergent alcohols of the present invention include $C_{11}$ and $C_{21}$ detergent alcohols comprising two, three, four or five methyl or ethyl branches or mixtures thereof. These can come via structures of diisoprenes and tetra isoprenes or other poly-branched poly-olefin feedstocks. They may be used in shampoos, dishwashing and/or hard surface cleaners once converted to the corresponding surfactant compositions. Examples of these alcohols are shown below. Useful embodiments will have high levels of methyl branching, and will comprise greater than 70% two, three or four methyl groups or mixtures thereof.

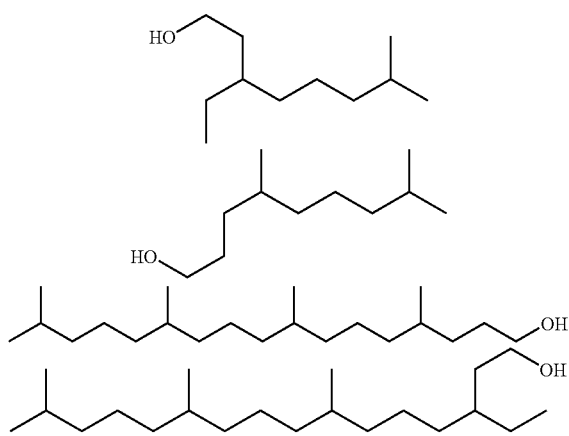

Other useful embodiments include poly-branched detergent alcohols compositions are acyclic and have a carbon atom chain length of 16. The embodiments may have greater than 10% trimethyl branching, or greater than 30% trimethyl branching or even 70% or more trimethyl branching.

Embodiment of poly-branched detergent alcohols derived from naturally derived farnesene extracted from pre-existing plants and organisms, farnesene obtained via genetically modified organisms, synthetically derived trimers of isoprene, mixtures thereof have been found to be useful in cleaning compositions. Poly-branched detergent alcohols and mixtures there of may be derived from mixtures of farnesene isomers.

Although it should be understood that any isoprene based olefin of any chain length can be used to prepare a detergent alcohol mixture using the process of the present invention as long as the derivatives come from oligomers obtained from acyclic isoprene like materials by any of the means described above. Examples of $C_{16}$ poly-branched detergent alcohols are illustrated below.

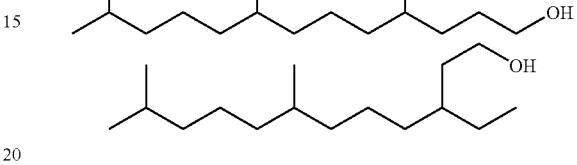

The polybranched detergent alcohols of the present invention include alcohols having one or more alcohol group. The processes of the present invention may be optimized to control a minimized or maximized formation of a poly alcohol (di, tri and tetra alcohols) as opposed to the monoalcohol.

SYNTHESIS EXAMPLE XII

Using Process Scheme I

Synthesis of Farnesene Derived Poly-Branched Polyalcohols 1.17 mmol of Dicobalt Octacarbonyl and 4.7 mmol of Eicosyl Phobane (a mixture of isomers [13887-00-8] and [13886-99-2]) are combined in 48 mls of dried, degassed 2-propyl alcohol in a 300 mL stainless steel pressure vessel that has a glass liner and PTFE coated stir bar. 47.7 mmol of the trans-beta-Farnesene (previously dried over mole sieves and filtered) are added to a feed tube attached to the reactor. The reactor lines are purged of air using vacuum and nitrogen cycles. The reactor is then purged with a 1:1 ratio mixture of carbon monoxide and hydrogen. The reactor containing the mixture of Dicobalt Octacarbonyl, Eicosyl Phobane, and 2-propyl alcohol is charged to an initial pressure of about 150 psig with the 1:1 ratio mixture of carbon monoxide and hydrogen. The reactor is heated to a temperature of from 60 to 65° C. with agitation at 150 to 200 rpm and the pressure is kept between 150 and 200 psig using the 1:1 ratio mixture of carbon monoxide and hydrogen. After 1 to 2 hours the reactor is cooled to below 40° C.

The reactor is vented and the contents of the feed tube (trans-beta-Farnesene) is charged to the reactor by opening the valves separating the two containers. The reactor is then charged with a new carbon monoxide-hydrogen mixture consisting of a 1:2 ratio mixture of carbon monoxide and hydrogen. The reactor is then heated to from 160 to 165° C. while keeping the pressure between 500 and 700 psig using a 1:2 ratio mixture of carbon monoxide and hydrogen.

The contents of the reactor are sampled with time and analyzed by GC to monitor the progress of the reaction. When the GC sample analysis indicates that the reaction is complete, the reaction mixture is cooled to room temperature and the carbon monoxide:hydrogen mixture is vented. The catalyst is removed and the resulting mixture contains greater than 30% diols and higher polyols. The diols and higher polyols are separated from the paraffins and mono alcohols by routine distillation procedure.

Poly-Branched Surfactants

Other embodiments of the present invention include surfactant compositions derived from the poly-branched detergent alcohols. These can be of $C_{11}$, $C_{16}$ or $C_{21}$ chain lengths and be poly-branched where the branches are methyl, ethyl or mixtures thereof. The surfactants may be formed by way of any alcohol-to-surfactant derivatization process known in the industry. They may include alcohol ethoxylates, alcohol sulfates or alcohol ethoxylated sulfates or mixtures thereof.

Examples of C11 and C21 poly-branched surfactants are:

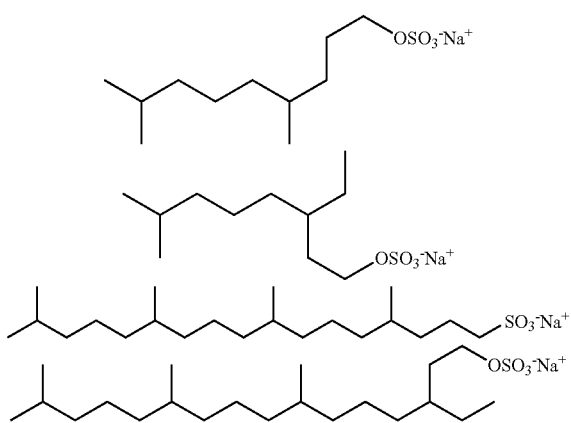

Other surfactant compositions may be derived from the acyclic $C_{16}$ poly-branched detergent alcohols and may include acyclic $C_{16}$ detergent alcohol ethoxylates, es or ethoxylated es. Non-limiting examples structures of preferred $C_{16}$ poly-branched alcohol surfactants are illustrated below:

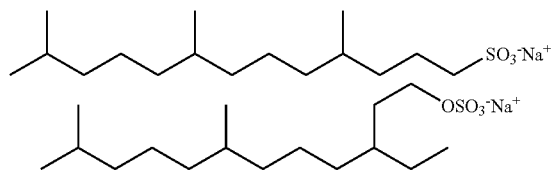

Mixtures of surfactants may also be desirable.

The alcohols of the invention can be alkoxylated using standard commercial and laboratory techniques and/or sulfated using any convenient sulfating agent, e.g., chlorosulfonic acid, $SO_3$/air, or oleum, to yield the final alcohol derived surfactant compositions.

The following examples define in detail the synthesis of the poly-branched surfactant compositions, the sixth embodiment of the invention:

SYNTHESIS EXAMPLE XIII

Synthesis of Farnesene Derived Poly-branched Alcohol Sulfate and Mixtures Thereof A reaction vessel that has agitation and a nitrogen purge to exclude air is used to combining 96 grams of the poly-branched alcohol material obtained in either SYNTHESIS EXAMPLES II, V or X and 149 grams of diethyl ether. The mixture is chilled to −5° C., then 50 grams of chlorosulfonic acid [7790-94-5] is added drop-wise while keeping the temperature of the mixture to below 10° C. Vacuum is applied to remove evolving HCl gas while the mixture was allowed to warm to ~30° C. Diethyl ether is replaced twice as it was evaporated while continuously mixing for two hours. Then the ether is removed by vacuum prior to the next step.

The resulting mixture is added slowly, with mixing, to a stainless steel beaker containing 287 grams of 9% sodium methoxide in methanol that was chilled in an ice bath. The mixture is stirred for an hour then poured into a stainless steel tray. The solvents are then evaporated and the sample further dried using a vacuum oven.

SYNTHESIS EXAMPLE XIV

Synthesis of Farnesene Derived 7-Mole Poly-branched Alcohol Ethoxylate (AE7) and Mixtures Thereof 200 grams of Farnesene derived alcohols (and other alcohols thereof prepared by any means or per SYNTHESIS EXAMPLE II) plus enough catalyst to facilitate the reaction of the alcohol with ethylene oxide within a suitable period of time and in a controllable manner are charged to a 600 mL stainless steel stirred pressure vessel with a cooling coil. A suitable catalyst is 1.1 grams of a solution consisting of 50% potassium hydroxide in water. Other kinds and quantities of catalyst can be used based upon the demands of the process.

The reactor is heated while applying a vacuum for removing materials that can result in side products, such as water, that may be introduced with the catalyst, at a temperature that will not allow the loss of the Farnesene alcohols, generally between 40° C. and 90° C., but preferably between about 60° C. and about at 80° C., when using a water aspirator as a vacuum source. The removal of water is facilitated by using low speed agitation, generally about 50 rpm, while sparging the mixture with a low level (trickle) stream of inert gas either through a bottom drain valve or through a stainless steel gas dispersion frit or any inert dip-tube or sintered metal fritted material or by sweeping the area above the mixture with inert gas. Samples can be drawn from the reactor and analyzed for water content using an appropriate analytical method such as Karl-Fischer titration.

After completion of the water removal step, ethylene oxide is added to the reactor. Ethylene oxide can be added all at once if the reactor system is properly designed to prevent an uncontrolled rate of reaction. However, the best reaction control is obtained by first heating the reactor under a static vacuum (or optionally with added pressure from an inert gas such as nitrogen) to a temperature that is suitable for the reaction of the alcohol-catalyst mixture with ethylene oxide to occur with minimum side products and color generation, generally between 85° and 150° C., but preferably between about 110° C. and 130° C.

Once the reactor has reached the desired temperature, 254 grams of ethylene oxide is added at a rate that will be controllable by the cooling system, generally over a period of 30 to 60 minutes. After the addition of ethylene oxide is completed, stirring and heating is continued until the ethylene oxide has been consumed by the reaction.

SYNTHESIS EXAMPLE XV

Synthesis of Farnesene Derived 10-Mole Poly-branched Alcohol Ethoxylate (AE10) and Mixtures Thereof The equipment and procedure from EXAMPLE XIII is used but the amount of ethylene oxide used is 363 grams in order to produce a Farnesene derived 10-mole poly-branched alcohol ethoxylate.

Synthesis EXAMPLE XVI

Synthesis of Farnesene Derived 3-Mole Polybranched Alcohol Ethoxylate (AE3) and Mixtures Thereof The equipment and procedure from EXAMPLE XIII is used but the amount of ethylene oxide used is 109 grams in order to produce a Farnesene derived 3-mole poly-branched alcohol ethoxylate.

SYNTHESIS EXAMPLE XVII

Synthesis of Farnesene Derived Poly-branched Alcohol Ethoxylate Sulfate (AE3S) and Mixtures Thereof A reaction vessel that has agitation and a nitrogen purge to exclude air is used while combining 62 grams of the material obtained in EXAMPLE XV and 149 grams of diethyl ether. The mixture is chilled to −5° C., then 50 grams of chlorosulfonic acid [7790-94-5] is added drop-wise while keeping the temperature of the mixture to below 10° C. Vacuum is applied to remove evolving HCl gas while the mixture is allowed to warm to ~30° C. Diethyl ether is replaced twice as it is evaporated while continuously mixing for two hours. Then the ether is removed by vacuum prior to the next step.

The mixture from above is added slowly with mixing to a stainless steel beaker containing 287 grams of 9% sodium methoxide in methanol that is chilled in an ice bath. The mixture is stirred for an hour then poured into a stainless steel tray. The solvents are then evaporated and the sample further dried using a vacuum oven.

SYNTHESIS EXAMPLE XVIII

Synthesis of 3-Ethyl-7,11-dimethyl-dodecanal and Mixtures Thereof

The equipment and procedure from EXAMPLE I is used, however the starting Farnesene used is 336 grams of trans-beta-Farnesene [18794-84-8]. The product may be used directly in EXAMPLE XIX.

EXAMPLE XIX

Synthesis of 3-Ethyl-7,11-dimethyl-dodecan-1-ol and Mixtures Thereof

The equipment and procedure from SYNTHESIS EXAMPLE II is used. However, the feed for the reaction is obtained from the process of SYNTHESIS EXAMPLE XVIII above, which uses trans-beta-Farnesene. The final reaction mixture is filtered through a 0.5 micron filter to remove catalyst. The resulting mixture is evaporated away from any non-volatile contaminants including catalyst residues by using a short-path distillation column at temperatures up to 250° C. and using a vacuum source as low as 1 torr. The crude distillate is then fractionally distilled using an Oldershaw column (WILMAD-LABGLASS Part #: G-2008-015J) while collecting small volume distilled fractions of 30 to 45 grams each at temperatures up to 350° C. and using a vacuum source as low as 5 torr. These fractions are analyzed by GC using a Restek RTX-5 capillary GC column (Cat #: 10244).

SYNTHESIS EXAMPLE XX

Synthesis of 3-Ethyl-7,11-dimethyl-dodecan-1-ol Alcohol Sulfate and Mixtures Thereof The equipment and procedure from SYNTHESIS EXAMPLE III is used. However, the alcohol used is the 3-Ethyl-7,11-dimethyl-dodecan-1-ol obtained in EXAMPLE XIX above. The product is analyzed by NMR and mass spectrometry and the resulting analysis is consistent with the predicted product 3-Ethyl-7,11-dimethyl-dodecan-1-ol Alcohol Sulfate.

Surfactant Compositions and Products Using the Poly-Branched Detergent Alcohol Derivatives and Surfactant Compositions The poly-branched surfactant composition comprising one or more derivatives of the detergent alcohol selected from the sulfate, alkoxylated or the alkoxylated sulfate or mixtures thereof according to the present invention are outstandingly suitable as a soil detachment-promoting additives for laundry detergents and cleaning compositions. They exhibit high dissolving power especially in the case of greasy soil. It is of particular advantage that they display the soil-detaching power even at low washing temperatures.

The surfactant composition comprising one or more derivatives of the novel poly-branched detergent alcohols selected from the sulfate, alkoxylated or the alkoxylated sulfate or mixtures thereof according to the present invention are outstandingly suitable as a soil detachment-promoting additives for laundry detergents and cleaning compositions. They exhibit high dissolving power especially in the case of greasy soil. It is of particular advantage that they display the soil-detaching power even at low washing temperatures.

The poly-branched surfactant compositions according to the present invention can be added to the laundry detergents and cleaning compositions in amounts of generally from 0.05 to 70% by weight, preferably from 0.1 to 40% by weight and more preferably from 0.25 to 10% by weight, based on the particular overall composition.

In addition, the laundry detergents and cleaning compositions generally comprise surfactants and, if appropriate, other polymers as washing substances, builders and further customary ingredients, for example cobuilders, complexing agents, bleaches, standardizers, graying inhibitors, dye transfer inhibitors, enzymes and perfumes.

The novel surfactant compositions of the present invention may be utilized in laundry detergents or cleaning compositions comprising a surfactant system comprising $C_{10}$-$C_{15}$ alkyl benzene sulfonates (LAS) and one or more co-surfactants selected from nonionic, cationic, anionic or mixtures thereof. The selection of co-surfactant may be dependent upon the desired benefit. In one embodiment, the co-surfactant is selected as a nonionic surfactant, preferably $C_{12}$-$C_{18}$ alkyl ethoxylates. In another embodiment, the co-surfactant is selected as an anionic surfactant, preferably $C_{10}$-$C_{18}$ alkyl alkoxy es ($AE_xS$) wherein x is from 1-30. In another embodiment the co-surfactant is selected as a cationic surfactant, preferably dimethyl hydroxyethyl lauryl ammonium chloride. If the surfactant system comprises $C_{10}$-$C_{15}$ alkyl benzene sulfonates (LAS), the LAS is used at levels ranging from about 9% to about 25%, or from about 13% to about 25%, or from about 15% to about 23% by weight of the composition.

The surfactant system may comprise from 0% to about 7%, or from about 0.1% to about 5%, or from about 1% to about 4% by weight of the composition of a co-surfactant selected from a nonionic co-surfactant, cationic co-surfactant, anionic co-surfactant and any mixture thereof.

Non-limiting examples of nonionic co-surfactants include: $C_{12}$-$C_{18}$ alkyl ethoxylates, such as, NEODOL® nonionic surfactants from Shell; $C_6$-$C_{12}$ alkyl phenol a wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block alkyl polyamine ethoxylates such as PLURONIC® from BASF; $C_{14}$-$C_{22}$ mid-chain branched alcohols, BA, as discussed in U.S. Pat. No. 6,150,322; $C_{14}$-$C_{22}$ mid-chain branched alkyl alkoxylates, $BAE_x$, wherein x is from 1-30, as discussed in U.S. Pat. No. 6,153,577, U.S. Pat. No. 6,020,303 and U.S. Pat. No. 6,093,856; alkylpolysaccharides as discussed in U.S. Pat. No. 4,565,647 Llenado, issued Jan. 26, 1986; specifically alkylpolyglycosides as discussed in U.S. Pat. No. 4,483,780 and U.S. Pat. No. 4,483,779; polyhydroxy detergent acid amides as discussed in U.S. Pat. No. 5,332,528; and ether capped poly(oxyalkylated) alcohol surfactants as discussed in U.S. Pat. No. 6,482,994 and WO 01/42408.

Non-limiting examples of semi-polar nonionic co-surfactants include: water-soluble amine oxides containing one alkyl moiety of from about 10 to about 18 carbon atoms and 2 moieties selected from the group consisting of alkyl moieties and hydroxyalkyl moieties containing from about 1 to about 3 carbon atoms; water-soluble phosphine oxides containing one alkyl moiety of from about 10 to about 18 carbon atoms and 2 moieties selected from the group consisting of alkyl moieties and hydroxyalkyl moieties containing from about 1 to about 3 carbon atoms; and water-soluble sulfoxides containing one alkyl moiety of from about 10 to about 18 carbon atoms and a moiety selected from the group consisting of alkyl moieties and hydroxyalkyl moieties of from about 1 to about 3 carbon atoms. See WO 01/32816, U.S. Pat. No. 4,681,704, and U.S. Pat. No. 4,133,779.

Non-limiting examples of cationic co-surfactants include: the quaternary ammonium surfactants, which can have up to 26 carbon atoms include: alkoxylate quaternary ammonium (AQA) surfactants as discussed in U.S. Pat. No. 6,136,769; dimethyl hydroxyethyl quaternary ammonium as discussed in 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022,844; and amino surfactants as discussed in U.S. Pat. No. 6,221,825 and WO 00/47708, specifically amido propyldimethyl amine (APA).

Nonlimiting examples of anionic co-surfactants useful herein include: $C_{10}$-$C_{20}$ primary, branched chain and random alkyl es (AS); $C_{10}$-$C_{18}$ secondary (2,3) alkyl es; $C_{10}$-$C_{18}$ alkyl alkoxy es ($AE_xS$) wherein x is from 1-30; $C_{10}$-$C_{18}$ alkyl alkoxy carboxylates comprising 1-5 ethoxy units; mid-chain branched alkyl es as discussed in U.S. Pat. No. 6,020,303 and U.S. Pat. No. 6,060,443; mid-chain branched alkyl alkoxy es as discussed in U.S. Pat. No. 6,008,181 and U.S. Pat. No. 6,020,303; modified alkylbenzene sulfonate (MLAS) as discussed in WO 99/05243, WO 99/05242 and WO 99/05244; methyl ester sulfonate (MES); and alpha-olefin sulfonate (AOS).

The present invention may also relates to compositions comprising the inventive surfactant composition of the sixth embodiment and a seventh embodiment, a surfactant composition comprising $C_8$-$C_{18}$ linear alkyl sulfonate surfactant and a co-surfactant. The compositions can be in any form, namely, in the form of a liquid; a solid such as a powder, granules, agglomerate, paste, tablet, pouches, bar, gel; an emulsion; types delivered in dual-compartment containers; a spray or foam detergent; premoistened wipes (i.e., the cleaning composition in combination with a nonwoven material such as that discussed in U.S. Pat. No. 6,121,165, Mackey, et al.); dry wipes (i.e., the cleaning composition in combination with a nonwoven materials, such as that discussed in U.S. Pat. No. 5,980,931, Fowler, et al.) activated with water by a consumer; and other homogeneous or multiphase consumer cleaning product forms.

In embodiment seven, the cleaning composition of the present invention is a liquid or solid laundry detergent composition. In another seventh embodiment, the cleaning composition of the present invention is a hard surface cleaning composition, preferably wherein the hard surface cleaning composition impregnates a nonwoven substrate. As used herein "impregnate" means that the hard surface cleaning composition is placed in contact with a nonwoven substrate such that at least a portion of the nonwoven substrate is penetrated by the hard surface cleaning composition, preferably the hard surface cleaning composition saturates the nonwoven substrate. The cleaning composition may also be utilized in car care compositions, for cleaning various surfaces such as hard wood, tile, ceramic, plastic, leather, metal, glass. This cleaning composition could be also designed to be used in a personal care and pet care compositions such as shampoo composition, body wash, liquid or solid soap and other cleaning composition in which surfactant comes into contact with free hardness and in all compositions that require hardness tolerant surfactant system, such as oil drilling compositions.

In another seventh embodiment the cleaning composition is a dish cleaning composition, such as liquid hand dishwashing compositions, solid automatic dishwashing compositions, liquid automatic dishwashing compositions, and tab/unit does forms of automatic dishwashing compositions.

Quite typically, cleaning compositions herein such as laundry detergents, laundry detergent additives, hard surface cleaners, synthetic and soap-based laundry bars, fabric softeners and fabric treatment liquids, solids and treatment articles of all kinds will require several adjuncts, though certain simply formulated products, such as bleach additives, may require only, for example, an oxygen bleaching agent and a surfactant as described herein. A comprehensive list of suitable laundry or cleaning adjunct materials can be found in WO 99/05242.

Common cleaning adjuncts include builders, enzymes, polymers not discussed above, bleaches, bleach activators, catalytic materials and the like excluding any materials already defined hereinabove. Other cleaning adjuncts herein can include suds boosters, suds suppressors (antifoams) and the like, diverse active ingredients or specialized materials such as dispersant polymers (e.g., from BASF Corp. or Rohm & Haas) other than those described above, color speckles, silvercare, anti-tarnish and/or anti-corrosion agents, dyes, fillers, germicides, alkalinity sources, hydrotropes, anti-oxidants, enzyme stabilizing agents, pro-perfumes, perfumes, solubilizing agents, carriers, processing aids, pigments, and, for liquid formulations, solvents, chelating agents, dye transfer inhibiting agents, dispersants, brighteners, suds suppressors, dyes, structure elasticizing agents, fabric softeners, anti-abrasion agents, hydrotropes, processing aids, and other fabric care agents, surface and skin care agents. Suitable examples of such other cleaning adjuncts and levels of use are found in U.S. Pat. Nos. 5,576,282, 6,306,812 B1 and 6,326,348 B1.

Method of Use

The present invention includes a method for cleaning a targeted surface. As used herein "targeted surface" may include such surfaces such as fabric, dishes, glasses, and other cooking surfaces, hard surfaces, hair or skin. As used herein "hard surface" includes hard surfaces being found in a typical home such as hard wood, tile, ceramic, plastic, leather, metal, glass. Such method includes the steps of contacting the composition comprising the modified polyol compound, in neat form or diluted in wash liquor, with at least a portion of a targeted surface then optionally rinsing the targeted surface. Preferably the targeted surface is subjected to a washing step prior to the aforementioned optional rinsing step. For purposes of the present invention, washing includes, but is not limited to, scrubbing, wiping and mechanical agitation.

As will be appreciated by one skilled in the art, the cleaning compositions of the present invention are ideally suited for use in home care (hard surface cleaning compositions) and/or laundry applications.

The composition solution pH is chosen to be the most complimentary to a target surface to be cleaned spanning broad range of pH, from about 5 to about 11. For personal care such as skin and hair cleaning pH of such composition preferably has a pH from about 5 to about 8 for laundry cleaning compositions pH of from about 8 to about 10. The compositions are preferably employed at concentrations of from about 200 ppm to about 10,000 ppm in solution. The water temperatures preferably range from about 5° C. to about 100° C.

For use in laundry cleaning compositions, the compositions are preferably employed at concentrations from about 200 ppm to about 10000 ppm in solution (or wash liquor). The water temperatures preferably range from about 5° C. to about 60° C. The water to fabric ratio is preferably from about 1:1 to about 20:1.

The method may include the step of contacting a nonwoven substrate impregnated with an embodiment of the composition of the present invention As used herein "nonwoven substrate" can comprise any conventionally fashioned nonwoven sheet or web having suitable basis weight, caliper (thickness), absorbency and strength characteristics. Examples of suitable commercially available nonwoven substrates include those marketed under the tradename SONTARA® by DuPont and POLYWEB® by James River Corp.

As will be appreciated by one skilled in the art, the cleaning compositions of the present invention are ideally suited for use in liquid dish cleaning compositions. The method for using a liquid dish composition of the present invention comprises the steps of contacting soiled dishes with an effective amount, typically from about 0.5 ml. to about 20 ml. (per 25 dishes being treated) of the liquid dish cleaning composition of the present invention diluted in water.

Composition Formulations

EXAMPLE XXI

Granular Laundry Detergent

| Formula | A wt % | B wt % | C wt % | D wt % | E wt % |
|---|---|---|---|---|---|
| Poly-branched Surfactant according to SYNTHETIC EXAMPLES XIII through XX based on the poly-alcohols of SYNTHETIC EXAMPLE XII | 13-25 | 13-25 | 13-25 | 13-25 | 9-25 |
| $C_{12-18}$ Ethoxylate e | — | — | 0-3 | — | 0-1 |
| $C_{14-15}$ alkyl ethoxylate (EO = 7) | 0-3 | 0-3 | — | 0-5 | 0-3 |
| Dimethyl hydroxyethyl lauryl ammonium chloride | — | — | 0-2 | 0-2 | 0-2 |
| $C_{8\text{-}10}\!-\!\underset{\underset{CH_3}{\mid}}{\overset{\overset{CH_3}{\mid}}{N^+}}\!-\!(CH_2CH_2)OH$ | 20-40 | — | 18-33 | 12-22 | 0-15 |
| Sodium tripolyphosphate K1 | | | | | |
| Zeolite | 0-10 | 20-40 | 0-3 | — | — |
| Silicate builder | 0-10 | 0-10 | 0-10 | 0-10 | 0-10 |
| Carbonate | 0-30 | 0-30 | 0-30 | 5-25 | 0-20 |
| Diethylene triamine penta acetate | 0-1 | 0-1 | 0-1 | 0-1 | 0-1 |
| Polyacrylate | 0-3 | 0-3 | 0-3 | 0-3 | 0-3 |
| Carboxy Methyl Cellulose | 0.2-0.8 | 0.2-0.8 | 0.2-0.8 | 0.2-0.8 | 0.2-0.8 |
| Percarbonate | 0-10 | 0-10 | 0-10 | 0-10 | 0-10 |
| Nonanoyloxybenzenesulfonate | — | — | 0-2 | 0-2 | 0-2 |
| Tetraacetylethylenediamine | — | — | 0-0.6 | 0-0.6 | 0-0.6 |
| Zinc Phthalocyanine Tetrasulfonate | — | — | 0-0.005 | 0-0.005 | 0-0.005 |
| Brightener | 0.05-0.2 | 0.05-0.2 | 0.05-0.2 | 0.05-0.2 | 0.05-0.2 |
| $MgSO_4$ | — | — | 0-0.5 | 0-0.5 | 0-0.5 |
| Enzymes | 0-0.5 | 0-0.5 | 0-0.5 | 0-0.5 | 0-0.5 |
| Minors (perfume, dyes, suds stabilizers) | balance | balance | balance | balance | balance |

EXAMPLE XXII

Granular Laundry Detergent

Aqueous Slurry Composition.

| Component | % w/w Aqueous slurry |
|---|---|
| A compound having the following general structure: bis(($C_2H_5O$)($C_2H_4O$)n)($CH_3$)—$N^+$—$C_xH_{2x}$—$N^+$—($CH_3$)—bis(($C_2H_5O$)($C_2H_4O$)n), wherein n = from 20 to 30, and x = from 3 to 8, or sulfated or sulphonated variants thereof | 1.23 |
| Ethylenediamine disuccinic acid | 0.35 |
| Brightener | 0.12 |
| Magnesium sulfate | 0.72 |
| Acrylate/maleate copolymer | 6.45 |
| Linear alkyl benzene sulphonate | 11.92 |
| Hydroxyethane di(methylene phosphonic acid) | 0.32 |
| Sodium carbonate | 4.32 |
| Sodium sulfate | 47.49 |

-continued

| Component | % w/w Aqueous slurry |
|---|---|
| Soap | 0.78 |
| Water | 24.29 |
| Miscellaneous | 0.42 |
| Total Parts | 100.00 |

Preparation of a Spray-Dried Powder.

An aqueous slurry having the composition as described above is prepared having a moisture content of 25.89%. The aqueous slurry is heated to 72° C. and pumped under high pressure (from $5.5 \times 10^6 Nm^{-2}$ to $6.0 \times 10^6 Nm^{-2}$), into a counter current spray-drying tower with an air inlet temperature of from 270° C. to 300° C. The aqueous slurry is atomised and the atomised slurry is dried to produce a solid mixture, which is then cooled and sieved to remove oversize material (>1.8 mm) to form a spray-dried powder, which is free-flowing. Fine material (<0.15 mm) is elutriated with the exhaust the exhaust air in the spray-drying tower and collected in a post tower containment system. The spray-dried powder has a moisture content of 1.0 wt %, a bulk density of 427 g/l and a particle size distribution such that 95.2 wt % of the spray-dried powder has a particle size of from 150 to 710 micrometers. The composition of the spray-dried powder is given below.

Spray-Dried Powder Composition.

| Component | % w/w Spray-dried powder |
|---|---|
| A compound having the following general structure: bis$((C_2H_5O)(C_2H_4O)n)(CH_3)$—$N^+$—$C_xH_{2x}$—$N^+$—$(CH_3)$-bis$((C_2H_5O)(C_2H_4O)n)$, wherein n = from 20 to 30, and x = from 3 to 8, or sulfated or sulphonated variants thereof | 1.62 |
| Ethylenediamine disuccinic acid | 0.46 |
| Brightener | 0.16 |
| Magnesium sulfate | 0.95 |
| Acrylate/maleate copolymer | 8.45 |
| Linear alkyl benzene sulphonate blended with Poly-branched Surfactant of SYNTHETIC EXAMPLES XIII through XX | 12.65 |
| Hydroxyethane di(methylene phosphonic acid) | 0.42 |
| Sodium carbonate | 5.65 |
| Sodium sulfate | 61.98 |
| Soap | 1.02 |
| Water | 1.00 |
| Miscellaneous | 0.55 |
| Total Parts | 100.00 |

Preparation of an Anionic Surfactant Particle 1

The anionic detersive surfactant particle 1 is made on a 520 g batch basis using a Tilt-A-Pin then Tilt-A-Plow mixer (both made by Processall). 108 g sodium sulfate supplied is added to the Tilt-A-Pin mixer along with 244 g sodium carbonate. 168 g of 70% active $C_{25}E_3S$ paste (sodium ethoxy sulfate based on $C_{12/15}$ alcohol and ethylene oxide) is added to the Tilt-A-Pin mixer. The components are then mixed at 1200 rpm for 10 seconds. The resulting powder is then transferred into a Tilt-A-Plow mixer and mixed at 200 rpm for 2 minutes to form particles. The particles are then dried in a fluid bed dryer at a rate of 2500 l/min at 120° C. until the equilibrium relative humidity of the particles is less than 15%. The dried particles are then sieved and the fraction through 1180 µm and on 250 µm is retained The composition of the anionic detersive surfactant particle 1 is as follows:

25.0% w/w $C_{25}E_3S$ sodium ethoxy sulfate 18.0% w/w sodium sulfate 57.0% w/w sodium carbonate Preparation of a Cationic Detersive Surfactant Particle 1

The cationic surfactant particle 1 is made on a 14.6 kg batch basis on a Morton FM-50 Loedige mixer. 4.5 kg of micronised sodium sulfate and 4.5 kg micronised sodium carbonate are premixed in the Morton FM-50 Loedige mixer. 4.6 kg of 40% active mono-$C_{12-14}$ alkyl mono-hydroxyethyl di-methyl quaternary ammonium chloride (cationic surfactant) aqueous solution is added to the Morton FM-50 Loedige mixer whilst both the main drive and the chopper are operating. After approximately two minutes of mixing, a 1.0 kg 1:1 weight ratio mix of micronised sodium sulfate and micronised sodium carbonate is added to the mixer. The resulting agglomerate is collected and dried using a fluid bed dryer on a basis of 2500 l/min air at 100-140° C. for 30 minutes. The resulting powder is sieved and the fraction through 1400 µm is collected as the cationic surfactant particle 1. The composition of the cationic surfactant particle 1 is as follows:

15% w/w mono-$C_{12-14}$ alkyl mono-hydroxyethyl di-methyl quaternary ammonium chloride 40.76% w/w sodium carbonate 40.76% w/w sodium sulfate 3.48% w/w moisture and miscellaneous Preparation of a Granular Laundry Detergent Composition 10.84 kg of the spray-dried powder of example 6, 4.76 kg of the anionic detersive surfactant particle 1, 1.57 kg of the cationic detersive surfactant particle 1 and 7.83 kg (total amount) of other individually dosed dry-added material are dosed into a 1 m diameter concrete batch mixer operating at 24 rpm. Once all of the materials are dosed into the mixer, the mixture is mixed for 5 minutes to form a granular laundry detergent composition. The formulation of the granular laundry detergent composition is described below:

A Granular Laundry Detergent Composition.

| Component | % w/w granular laundry detergent composition |
|---|---|
| Spray-dried powder from earlier table in Example 6 | 43.34 |
| 91.6 wt % active linear alkyl benzene sulphonate flake supplied by Stepan under the tradename Nacconol 90G ® | 0.22 |
| Citric acid | 5.00 |
| Sodium percarbonate (having from 12% to 15% active AvOx) | 14.70 |
| Photobleach particle | 0.01 |
| Lipase (11.00 mg active/g) | 0.70 |
| Amylase (21.55 mg active/g) | 0.33 |
| Protease (56.00 mg active/g) | 0.43 |
| Tetraacetyl ethylene diamine agglomerate (92 wt % active) | 4.35 |
| Suds suppressor agglomerate (11.5 wt % active) | 0.87 |
| Acrylate/maleate copolymer particle (95.7 wt % active) | 0.29 |
| Green/Blue carbonate speckle | 0.50 |
| Anionic detersive surfactant particle 1 | 19.04 |
| Cationic detersive surfactant particle 1 | 6.27 |
| Sodium sulfate | 3.32 |
| Solid perfume particle | 0.63 |
| Total Parts | 100.00 |

EXAMPLE XXII

Liquid Laundry Detergents

| Ingredient | A wt % | B wt % | C wt % | D wt % | E wt % |
|---|---|---|---|---|---|
| Sodium alkyl ether e | 14.4% | | 9.2% | 5.4% | |
| Poly-branched Surfactant according to SYNTHETIC EXAMPLES XIII through XX based on the polyalcohols of SYNTHETIC EXAMPLE XII | 4.4% | 12.2% | 5.7% | 1.3% | |
| Alkyl ethoxylate | 2.2% | 8.8% | 8.1% | 3.4% | |
| Amine oxide | 0.7% | 1.5% | | | |
| Citric acid | 2.0% | 3.4% | 1.9% | 1.0% | 1.6% |
| Detergent acid | 3.0% | 8.3% | | | 16.0% |
| Protease | 1.0% | 0.7% | 1.0% | | 2.5% |
| Amylase | 0.2% | 0.2% | | | 0.3% |
| Lipase | | | 0.2% | | |
| Borax | 1.5% | 2.4% | 2.9% | | |
| Calcium and sodium formate | 0.2% | | | | |
| Formic acid | | | | | 1.1% |
| Sodium polyacrylate | | | | 0.2% | |
| Sodium polyacrylate copolymer | | | 0.6% | | |
| DTPA[1] | 0.1% | | | | 0.9% |
| DTPMP[2] | | 0.3% | | | |
| EDTA[3] | | | | 0.1% | |
| Fluorescent whitening agent | 0.15% | 0.2% | 0.12% | 0.12% | 0.2% |
| Ethanol | 2.5% | 1.4% | 1.5% | | |
| Propanediol | 6.6% | 4.9% | 4.0% | | 15.7% |
| Sorbitol | | | 4.0% | | |
| Ethanolamine | 1.5% | 0.8% | 0.1% | | 11.0% |
| Sodium hydroxide | 3.0% | 4.9% | 1.9% | 1.0% | |
| Sodium cumene sulfonate | | 2.0% | | | |
| Silicone suds suppressor | | 0.01% | | | |
| Perfume | 0.3% | 0.7% | 0.3% | 0.4% | 0.6% |
| Opacifier[4] | | 0.30% | 0.20% | | 0.50% |
| Water | balance 100.0% | balance 100.0% | balance 100.0% | balance 100.0% | balance 100.0% |

[1] diethylenetriaminepentaacetic acid, sodium salt
[2] diethylenetriaminepentakismethylenephosphonic acid, sodium salt
[3] ethylenediaminetetraacetic acid, sodium salt
[4] Acusol OP 301

| Ingredient | F wt % | G wt % | H wt % | I wt % | J wt % | K wt % |
|---|---|---|---|---|---|---|
| Alkylbenzene sulfonic acid | 7 | 7 | 4.5 | 1.2 | 1.5 | 12.5 |
| Sodium C12-14 alkyl ethoxy 3 e | 2.3 | 2.3 | 4.5 | 4.5 | 7 | 18 |
| Poly-branched Surfactant according to SYNTHETIC EXAMPLES XIII through XX based on the polyalcohols of SYNTHETIC EXAMPLE XII | 5 | 5 | 2.5 | 2.6 | 4.5 | 4 |
| C12 alkyl dimethyl amine oxide | — | 2 | — | — | — | — |
| C12-14 alkyl hydroxyethyl dimethyl ammonium chloride | — | — | — | 0.5 | — | — |
| C12-18 Detergent acid | 2.6 | 3 | 4 | 2.6 | 2.8 | 11 |
| Citric acid | 2.6 | 2 | 1.5 | 2 | 2.5 | 3.5 |
| Protease enzyme | 0.5 | 0.5 | 0.6 | 0.3 | 0.5 | 2 |
| Amylase enzyme | 0.1 | 0.1 | 0.15 | — | 0.05 | 0.5 |
| Mannanase enzyme | 0.05 | — | 0.05 | — | — | 0.1 |
| Diethylenetriaminepenta (methylenephosphonic) acid | 0.2 | 0.3 | — | — | 0.2 | — |
| Hydroxyethane diphosphonic acid | — | — | 0.45 | — | — | 1.5 |
| FWA | 0.1 | 0.1 | 0.1 | — | — | 0.2 |
| Solvents (1,2 propanediol, ethanol), stabilizers | 3 | 4 | 1.5 | 1.5 | 2 | 4.3 |
| Hydrogenated castor oil derivative structurant | 0.4 | 0.3 | 0.3 | 0.1 | 0.3 | — |
| Boric acid | 1.5 | 2 | 2 | 1.5 | 1.5 | 0.5 |
| Na formate | — | — | — | 1 | — | — |
| Reversible protease inhibitor[3] | — | — | 0.002 | — | — | — |
| Perfume | 0.5 | 0.7 | 0.5 | 0.5 | 0.8 | 1.5 |
| Buffers (sodium hydroxide, Monoethanolamine) | To pH 8.2 | | | | | |
| Water and minors (antifoam, aesthetics, . . .) | To 100 | | | | | |

| Ingredient | L wt % | M wt % | N wt % | O wt % | P wt % | Q wt % |
|---|---|---|---|---|---|---|
| Alkylbenzene sulfonic acid | 5.5 | 2.7 | 2.2 | 12.2 | 5.2 | 5.2 |
| Poly-branched Surfactant according to SYNTHETIC EXAMPLES XIII through XX based on the polyalcohols of SYNTHETIC EXAMPLE XII | 16.5 | 20 | 9.5 | 7.7 | 1.8 | 1.8 |
| Sodium C12-14 alkyl e | 8.9 | 6.5 | 2.9 | — | | |
| C12-14 alkyl 7-ethoxylate | | | | | 0.15 | 0.15 |
| C14-15 alkyl 8-ethoxylate | | | | | 3.5 | 3.5 |
| C12-15 alkyl 9-ethoxylate | 1.7 | 0.8 | 0.3 | 18.1 | — | — |
| C12-18 Detergent acid | 2.2 | 2.0 | — | 1.3 | 2.6 | 2.6 |
| Citric acid | 3.5 | 3.8 | 2.2 | 2.4 | 2.5 | 2.5 |
| Protease enzyme | 1.7 | 1.4 | 0.4 | — | 0.5 | 0.5 |
| Amylase enzyme | 0.4 | 0.3 | — | — | 0.1 | 0.1 |
| Mannanase enzyme | | | | | 0.04 | 0.04 |
| PEG-PVAc Polymer[1] | — | — | — | — | — | 0.3 |
| Ethoxyed Hexamethylene Diamine Dimethyl Quat | — | — | — | — | — | 0.7 |
| Diethylenetriaminepenta (methylenephosphonic) acid | | | | | 0.2 | 0.2 |
| FWA | — | — | — | — | .04 | .04 |
| Solvents (1,2 propanediol, ethanol, stabilizers | 7 | 7.2 | 3.6 | 3.7 | 1.9 | 1.9 |
| Hydrogenated castor oil derivative structurant | 0.3 | 0.2 | 0.2 | 0.2 | 0.35 | 0.35 |
| Polyacrylate | — | — | — | 0.1 | — | — |
| Polyacrylate copolymer[2] | — | — | — | 0.5 | — | — |
| Sodium carbonate | — | — | — | 0.3 | — | — |
| Sodium silicate | — | — | — | — | — | — |
| Borax | 3 | 3 | 2 | 1.3 | — | — |
| Boric acid | 1.5 | 2 | 2 | 1.5 | 1.5 | 1.5 |
| Perfume | 0.5 | 0.5 | 0.5 | 0.8 | 0.5 | 0.5 |
| Buffers (sodium hydroxide, monoethanolamine) | | | | | 3.3 | 3.3 |
| Water, dyes and miscellaneous | Balance | | | | | |

[1]PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2]Alco 725 (styrene/acrylate)

EXAMPLE XXIII

Liquid Dish Handwashing Detergents

| Composition | A | B |
|---|---|---|
| $C_{12-13}$ Natural AE0.6S | 270 | 240 |
| $C_{10-14}$ mid-branched Amine Oxide | — | 6.0 |
| Poly-branched Surfactant according to SYNTHETIC EXAMPLES XIII through XX based on the polyalcohols of SYNTHETIC EXAMPLE XII | 2.0 | 5.0 |
| $C_{12-14}$ Linear Amine Oxide | 6.0 | — |
| SAFOL ® 23 Amine Oxide | 1.0 | 1.0 |
| $C_{11}E_9$ Nonionic[1] | 2.0 | 2.0 |
| Ethanol | 4.5 | 4.5 |
| Sodium cumene sulfonate | 1.6 | 1.6 |
| Polypropylene glycol 2000 | 0.8 | 0.8 |
| NaCl | 0.8 | 0.8 |
| 1,3 BAC Diamine[2] | 0.5 | 0.5 |
| Suds boosting polymer[3] | 0.2 | 0.2 |
| Water | Balance | Balance |

[1]Nonionic may be either $C_{11}$ Alkyl ethoxylated surfactant containing 9 ethoxy groups.
[2]1,3, BAC is 1,3 bis(methylamine)-cyclohexane.
[3](N,N-dimethylamino)ethyl methacrylate homopolymer

EXAMPLE 11

Automatic Dishwasher Detergent

| | A | B | C | D | E |
|---|---|---|---|---|---|
| Polymer dispersant[2] | 0.5 | 5 | 6 | 5 | 5 |
| Carbonate | 35 | 40 | 40 | 35-40 | 35-40 |
| Sodium tripolyphosphate | 0 | 6 | 10 | 0-10 | 0-10 |
| Silicate solids | 6 | 6 | 6 | 6 | 6 |
| Bleach and bleach activators | 4 | 4 | 4 | 4 | 4 |
| Polymer[1] | 0.05-10 | 1 | 2.5 | 5 | 10 |
| Enzymes | 0.3-0.6 | 0.3-0.6 | 0.3-0.6 | 0.3-0.6 | 0.3-0.6 |
| Disodium citrate dihydrate | 0 | 0 | 0 | 2-20 | 0 |
| Poly-branched Surfactant according to SYNTHETIC EXAMPLES XIII through XX based on the polyalcohols of SYNTHETIC EXAMPLE XII | 0.8-5 | 0.8-5 | 0.8-5 | 0.8-5 | 0.8-5 |
| Water, e, perfume, dyes and other adjuncts | Balance to 100% | Balance to 100% | Balance to 100% | Balance to 100% | Balance to 100% |

[1]An amphiphilic alkoxylated polyalkylenimine polymer or any mixture of polymers according to any of Examples 1, 2, 3, or 4.
[2]Such as ACUSOL ® 445N available from Rohm & Haas or ALCOSPERSE ® from Alco.

Test Methods

The following two analytical methods for characterizing branching in the present invention surfactant compositions are useful:

Separation and Identification of Components in Detergent Alcohols (performed prior to alkoxylation or after hydrolysis of alcohol sulfate for analytical purposes). The position and length of branching found in the precursor detergent alcohol materials is determined by GC/MS techniques [see: D. J. Harvey, Biomed, Environ. Mass Spectrum (1989). 18(9), 719-23; D. J. Harvey, J. M. Tiffany, J. Chromatogr. (1984), 301(1), 173-87; K. A. Karlsson, B. E. Samuelsson, G. O, Steen, Chem. Phys. Lipids (1973), 11(1), 17-38].

Identification of Separated Detergent Alcohol Alkoxy e Components by MS/MS. The position and length of branching is also determinable by Ion Spray-MS/MS or FAB-MS/MS techniques on previously isolated detergent alcohol sulfate components.

The average total carbon atoms of the branched primary alkyl surfactants herein can be calculated from the hydroxyl value of the precursor detergent alcohol mix or from the hydroxyl value of the alcohols recovered by extraction after hydrolysis of the alcohol sulfate mix according to common procedures, such as outlined in "Bailey's Industrial Oil and Fat Products", Volume 2, Fourth Edition, edited by Daniel Swern, pp. 440-441.

Unless otherwise noted, all component or composition levels are in reference to the active level of that component or composition, and are exclusive of impurities, for example, residual solvents or by-products, which may be present in commercially available sources.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An asymmetric acyclic polyaldehyde having 11, 16 or 21 carbon atoms and comprising at least two aldehyde groups, at least three branches, and three or less carbon-carbon double bonds, wherein the acyclic polyaldehyde has a backbone comprising the longest carbon chain having a midpoint and one aldehyde group of the polyaldehyde is attached to the terminal carbon of the backbone and at least one additional aldehyde group is directly or indirectly attached to the backbone on the same side of the backbone midpoint as the terminal aldehyde group.

2. A composition of matter comprising at least one acyclic polyaldehyde comprising 16 carbon atoms, at least two aldehyde groups, at least three branches, and three or less carbon-carbon double bonds, wherein the acyclic polyaldehyde has a backbone comprising the longest carbon chain having a midpoint and one aldehyde group of the polyaldehyde is attached to the terminal carbon of the backbone and at least one additional aldehyde group is directly or indirectly attached to the backbone on the same side of the backbone midpoint as the terminal aldehyde group.

3. A composition of matter according to claim 2 wherein the acyclic polyaldehyde comprises one, two or three carbon-carbon double bonds and where the branches are methyl or ethyl or mixtures thereof.

4. A composition of matter according to claim 2 wherein the acyclic polyaldehyde is saturated and the branches are methyl, ethyl or mixtures thereof.

5. A asymmetric detergent polyalcohol composition comprising at least one acyclic polyalcohol having 11, 16, or 21 carbon atoms, also comprising at least two hydroxyl alcohol groups, at least three branches wherein the branches are methyl, ethyl or mixtures thereof, wherein the detergent polyalcohol has a backbone comprising the longest carbon chain having a midpoint and one alcohol group of the polyalcohol is attached to the terminal carbon of the backbone and at least one additional alcohol group is directly or indirectly attached to the backbone on the same side of the backbone midpoint as the terminal alcohol group.

6. A detergent polyalcohol composition according to claim 5, wherein the acyclic polyalcohol has 16 carbon atoms.

7. A detergent polyalcohol composition according to claim 5, wherein greater than about 10% of the branched polyalcohols are trimethyl branched alcohols.

8. A detergent polyalcohol composition according to claim 5; wherein greater than about 30% of the branched polyalcohols are trimethyl branched alcohols.

9. A detergent polyalcohol composition according to claim 5 wherein greater than about 70% of the branched polyalcohol alcohols are trimethyl branched alcohols.

10. A detergent polyalcohol composition according to claim 5 wherein the alcohol is derived from a process selected from the group consisting of:
    a. natural derived farnesene extracted from pre-existing plants and organisms;
    b. farnesene obtained via genetically modified organisms;
    c. synthetically derived trimers of isoprene; and
    d. mixtures thereof.

11. A surfactant composition comprising one or more surfactant derivatives of isomers of acyclic asymmetric detergent polyalcohols alcohol having 11, 16, or 21 carbon atoms, at least two hydroxyl alcohol groups, and two, three, four or five methyl or ethyl branches or mixtures thereof, wherein the acyclic polyalcohols each have a backbone comprising the longest carbon chain having a midpoint and one alcohol group of the polyalcohol is attached to the terminal carbon of the backbone and at least one additional alcohol group is directly or indirectly attached to the backbone on the same side of the backbone midpoint as the terminal alcohol group.

12. A surfactant composition according to claim 11 wherein greater than 70% of the acyclic surfactant derivatives comprise two, three or four methyl groups.

13. A surfactant composition according to claim 11 wherein the surfactant derivatives of the isomers of acyclic detergent polyalcohols are sulfated derivatives, ethoxylated derivatives, ethoxylated and sulfated derivatives, or mixtures thereof.

14. A cleaning composition comprising the surfactant composition according to claim 11.

15. A cleaning composition comprising the surfactant composition according to claim 12.

* * * * *

UNITED STATES PATENT AND TRADEMARK OFFICE
CERTIFICATE OF CORRECTION

| | | |
|---|---|---|
| PATENT NO. | : 7,994,369 B2 | Page 1 of 1 |
| APPLICATION NO. | : 12/564456 | |
| DATED | : August 9, 2011 | |
| INVENTOR(S) | : Scheibel et al. | |

It is certified that error appears in the above-identified patent and that said Letters Patent is hereby corrected as shown below:

<u>Column 38</u>

Line 12, after the word one, insert --asymmetric--.

Signed and Sealed this
Fifteenth Day of January, 2013

David J. Kappos
*Director of the United States Patent and Trademark Office*